United States Patent [19]

Shiozawa et al.

[11] Patent Number: 5,057,535
[45] Date of Patent: Oct. 15, 1991

[54] DERIVATIVES OF AN AMINOKETONE

[75] Inventors: Akira Shiozawa, Omiya; Michio Ishikawa, Tokyo; Giichi Izumi, Tokyo; Katsuhiko Sakitama, Tokyo; Kazuhisa Narita, Tokyo; Shuji Kurashige; Takeji Sakasai, both of Urawa; Kazuo Ohtsuki; Hideo Sugimura, both of Tokyo; Hirotaka Yamamoto, Yono, all of Japan

[73] Assignee: Nippon Kayaku Kabushiki Kaisha, Tokyo, Japan

[21] Appl. No.: 101,134

[22] Filed: Sep. 25, 1987

Related U.S. Application Data

[63] Continuation-in-part of Ser. No. 6,850,558, Apr. 11, 1986, abandoned.

[30] Foreign Application Priority Data

| Apr. 11, 1985 | [JP] | Japan | 60-75379 |
| May 28, 1985 | [JP] | Japan | 60-113103 |
| Jun. 19, 1985 | [JP] | Japan | 60-131629 |
| Dec. 4, 1985 | [JP] | Japan | 60-271381 |
| Oct. 9, 1986 | [JP] | Japan | 61-239115 |
| Oct. 9, 1986 | [JP] | Japan | 61-239116 |
| Aug. 11, 1987 | [JP] | Japan | 62-199086 |

[51] Int. Cl.$^5$ .................. A61K 31/40; C07D 295/108
[52] U.S. Cl. ..................................... 514/428; 548/571
[58] Field of Search ..................... 548/571; 514/428

[56] References Cited

U.S. PATENT DOCUMENTS

| 3,203,962 | 8/1965 | Huebner | 260/326.5 |
| 4,277,474 | 7/1981 | Kohda et al. | 544/175 X |

FOREIGN PATENT DOCUMENTS

| 4451779 | 8/1979 | Australia . |
| 7042381 | 11/1981 | Australia . |
| 5442486 | 9/1986 | Australia . |
| 0004000 | 9/1979 | European Pat. Off. . |
| 0105632 | 4/1984 | European Pat. Off. . |
| 156785 | 10/1985 | European Pat. Off. . |
| 0163537 | 12/1985 | European Pat. Off. . |
| 0193875 | 9/1986 | European Pat. Off. . |
| 0200942 | 11/1986 | European Pat. Off. . |
| 1301868 | 7/1962 | France . |
| 1213963 | 11/1970 | United Kingdom . |

OTHER PUBLICATIONS

JP-A-60 06 675, Chemical Abstracts, vol. 102, p. 571, Abstract No. 148887(Hokuriku).
Patent Abs. of Japan, vol. 9, No. 52, (C-269) [1775], Mar. 6, 1985.
Chawla et al., (1970) *Journal of Medicinal Chemistry*, vol. 13, No. 3, pp. 480-488.
Chem. Abstracts, vol. 52 (1958), 11067b-i, Nobles et al.
Chem. Abstracts, vol. 58 (1963), 5644b-g, Albrecht, et al.
Chem. Abstracts, vol. 60 (1964), 11987d-g, Ciba Ltd.
Chem. Abstracts, vol. 101 (1984), 38348m, Dainippon Pharmaceutical.
Chem. Abstracts, vol. 103 (1985), 98607w, Ito, et al.
Chem. Abstracts, vol. 100 (1984), 96478u, Nagai, et al.
Chem. Abstracts, vol. 96 (1982), 103860s, Knops, et al.
Chem. Abstracts, vol. 93 (1980), 46127v, Narayan, et al.
Chem. Abstracts, vol. 95 (1981), 149960g, Kohda, et al.
Chem. Abstracts, vol. 102 (1985), 160188v, Nagai, et al.

*Primary Examiner*—Joseph Paul Brust
*Attorney, Agent, or Firm*—Banner, Birch, McKie & Beckett

[57] ABSTRACT

A new class of aminoketone derivatives according to the formula:

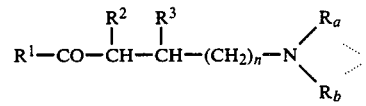

and certain propiophenone derivatives in particular, corresponding to the formula:

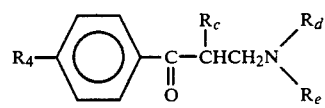

having central muscle relaxant activity.

11 Claims, No Drawings

DERIVATIVES OF AN AMINOKETONE

CROSS-REFERENCE TO RELATED APPLICATIONS

This application is a continuation-in-part of our now abandoned application Ser. No. 850,558 filed on Apr. 11, 1986.

BACKGROUND OF THE INVENTION

2-Methyl-1-(4-methylphenyl)-3-piperidino-1-propanone (generic name: tolperisone) is known as one of β-aminopropiophenone derivatives having a central muscle relaxant activity (G.B. 1,213,963). Tolperisone is widely used in Japan for the clinical treatment of spastic paralysis or motor palsy resulting from muscular hypertonia.

The potency and duration of tolperisone in its clinical use, however, are not always satisfactory, and the improvements thereof have been desired.

SUMMARY OF THE INVENTION

The object of this invention is to provide new aminoketone derivatives having a central muscle relaxant activity. The compounds of this invention effect for a long time and are also low in toxicity, so that their use as an excellent muscle relaxant is expected.

The new aminoketone derivatives according to this invention are represented by the following general formula (I):

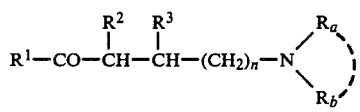

wherein $R^1$ and

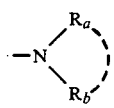

are the groups defined as I, II or III below, one of $R^2$ and $R^3$ is a hydrogen atom and the other is a lower alkyl group; n is 0 when $R^1$ is I or II, and it is 0 or 1 when $R^1$ is III: I: $R^1$ is a group selected from the groups ① to ⑦ mentioned below and

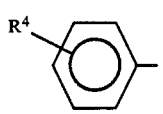

e,crc/1/ a group of the formula

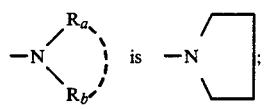

(wherein $R^4$ is a trihalogenomethyl group),
② a group of the formula

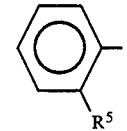

(wherein $R^5$ is a fluorine atom, a bromine atom, a lower alkoxyl group, a lower alkyl group, hydroxyl group, $CH_2=CH-$, a phenyl group or

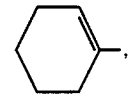

③ a group of the formula

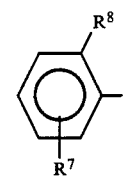

(wherein $R^6$ is a halogen atom, a lower alkyl group,

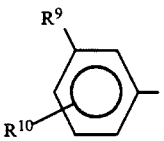

$CH_2=CH-$ or a phenyl group),
④ a group of the formula (wherein $R^7$ and $R^8$ each are halogen atoms, lower alkyl groups, lower alkoxyl groups or hydrogen atoms), ⑤ a group of the formula (wherein $R^9$ and $R^{10}$ each are halogen atoms, lower alkyl groups or lower alkoxyl group, and $R^{10}$ is a substituent at the position 4 or 5 of the phenyl ring),
⑥ a group of the formula

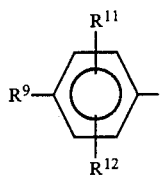

(wherein $R^9$ is a lower alkoxyl group, a lower alkyl group or a halogen atom; $R^{11}$ is a substituent at the position 2 or 3 of the phenyl ring, and is a lower alkyl group, a lower alkoxyl group or a hydroxyl group; and $R^{12}$ is a substituent at the position 5 or 6 of the phenyl ring, and is a lower alkyl group or a halogen atom), and ⑦ a group of the formula

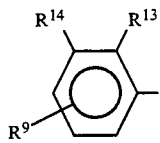

(wherein $R^9$ is a lower alkoxyl group, a lower alkyl group or a halogen atom; $R^{13}$ is a lower alkyl group, a lower alkoxyl group or a hydroxyl group; and $R^{14}$ is a lower alkyl group or a lower alkoxyl group, provided that $R^{14}$ is a lower alkoxyl group when $R^9$ is a lower alkoxyl group at the position 4 of the phenyl ring): II: $R^1$ is a group selected from the groups ① or ② mentioned below and

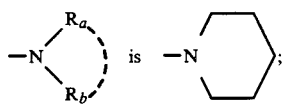

① a group of the formula

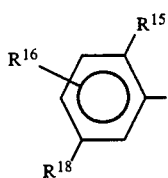

(wherein $R^{15}$ and $R^{16}$ each are lower alkyl groups or lower alkoxyl groups; and $R^{17}$ is a hydrogen atom or a lower alkoxyl group, provided that one of $R^{15}$ and $R^{16}$ is a lower alkoxyl group when $R^{17}$ is a lower alkoxyl group), ② a group of the formula

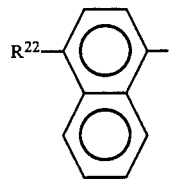

(wherein $R^{15}$ and $R^{16}$ each are lower alkyl groups or lower alkoxyl groups and $R^{18}$ is a lower alkyl group, provided that $R^{16}$ is a substituent at the position 3 or 4): III: $R^1$ is a group selected from the groups ①, ②, ③ or ④ mentioned below

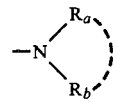

is a group of the formula

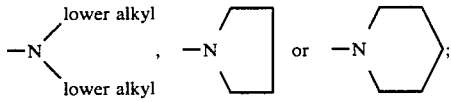

① a group of the formula

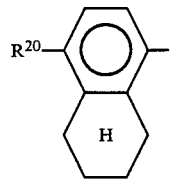

(wherein $R^{20}$ is a hydrogen atom, a halogen atom,

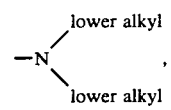

a lower alkyl group or a lower alkoxyl group),

② a group of the formula.

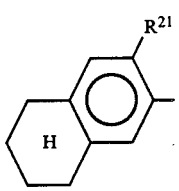

(wherein $R^{21}$ is a halogen atom, a lower alkyl group or a lower alkoxyl group), ③ a group of the formula

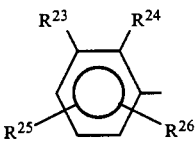

(wherein $R^{22}$ is a lower alkoxyl group), and

④ a group of the formula

(wherein $R^{23}$ is a halogen atom or a lower alkyl group, $R^{24}$ and $R^{25}$ each are lower alkyl groups, and $R^{26}$ is a lower alkyl group or a lower alkoxyl group).

The present invention also relates to the propiophenone derivatives represented by the following general formula (II) or salts thereof:

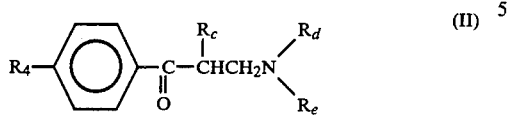

(wherein $R_c$ is a lower alkyl group, $R_d$ and $R_e$ are each a lower alkyl group or $R_d$ and $R_e$ are combined to represent a $C_4$-$C_5$ alkylene group, and $R_4$ is a trihalogenomethyl group).

DETAILED DESCRIPTION OF THE INVENTION

In the compounds of this invention represented by the above-shown formula, the lower alkyl group may be selected from $C_1$-$C_4$ alkyl groups, preferably $C_1$-$C_3$ alkyl groups, such as methyl, ethyl, n-propyl, isopropyl, n-butyl, isobutyl and the like.

The lower alkoxyl group may be selected from $C_1$-$C_4$, preferably $C_1$-$C_3$ alkoxyl groups such as methoxy, ethoxy, n-propoxy, isopropoxy, n-butoxy, tert-butoxy and the like.

The halogen atom may be a chlorine, bromine or fluorine atom.

The trihalogenomethyl group may be trichloromethyl, trifluoromethyl or the like.

Typical examples of the compounds of this invention are shown in Table I, Table II and Table II-2.

TABLE I $$R^1-CO-\underset{\underset{CH_3}{|}}{CH}-CH_2-N\diagup\diagdown$$

(Compounds represented by the general formula (I)

$$R^1-CO-\underset{\underset{R^2}{|}}{CH}-\underset{\underset{R^3}{|}}{CH}-(CH_2)_n-N\diagup\diagdown\underset{R_b}{\overset{R_a}{}}\text{ wherein } R^2 \text{ is a}$$

methyl group, $R^3$ is a hydrogen group, $n = $ zero, $-N\diagup\diagdown\underset{R_b}{\overset{R_a}{}}$ is a pyrrolidinyl group and $R^1$ is a substituent as defined in Table I below.)

| Compound No. | $R^1$ |
|---|---|
| 1-1 | 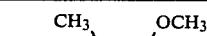 |

TABLE I-continued

| 1-3 | 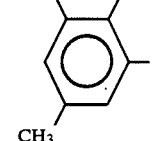 |
| 1-4 | 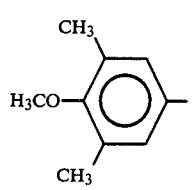 |
| 1-5 | 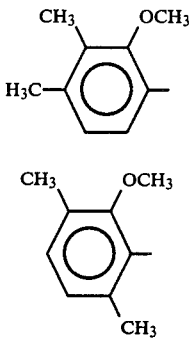 |
| 1-6 | |
| 1-7 | |
| 1-8 | 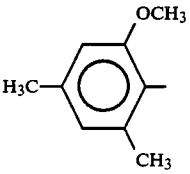 |
| 1-9 | 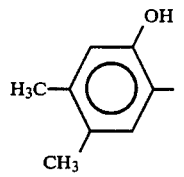 |
| 1-10 | 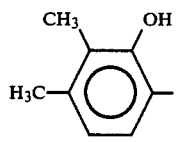 |
| 1-11 | 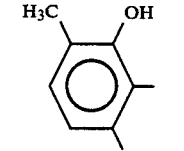 |

TABLE I-continued
| | | |
|---|---|---|
| 1-12 | 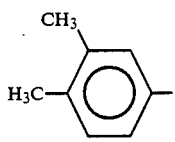 | |
| 1-13 | 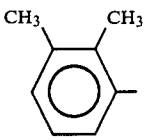 | |
| 1-14 | 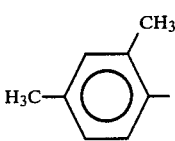 | |
| 1-15 | 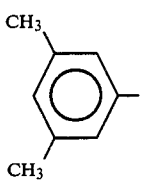 | |
| 1-16 | 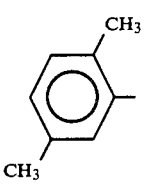 | |
| 1-17 | 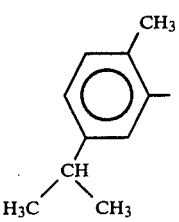 | |
| 1-18 | 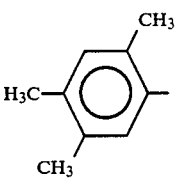 | |
| 1-19 | 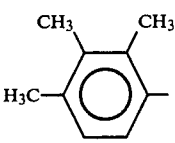 | |
| 1-20 | 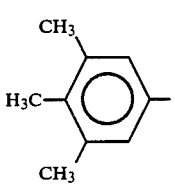 | |
TABLE I-continued
| | | |
|---|---|---|
| 1-21 | 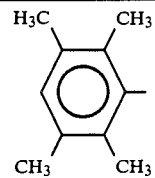 | |
| 3-1 | 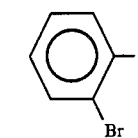 | |
| 3-2 | 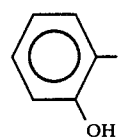 | |
| 3-3 | 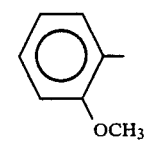 | |
| 3-4 | 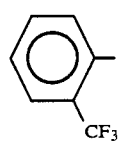 | |
| 3-5 | 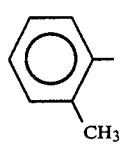 | |
| 3-6 | 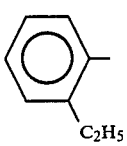 | |
| 3-7 | 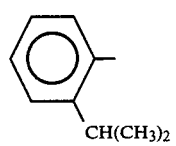 | |
| 3-8 | 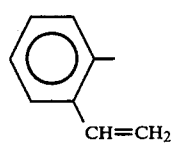 | |
| 3-9 | 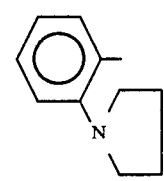 | |

TABLE I-continued
| | | |
|---|---|---|
| 3-10 | 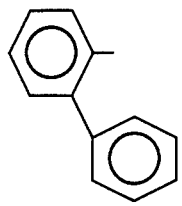 | |
| 3-11 | 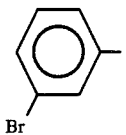 | |
| 3-12 | 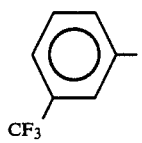 | |
| 3-13 | 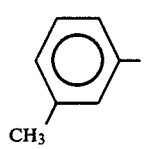 | |
| 3-14 |  | |
| 3-15 | 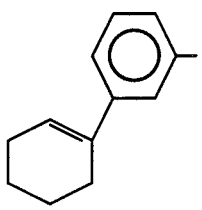 | |
| 3-16 | 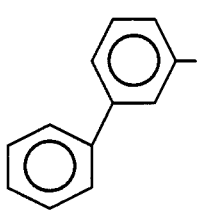 | |
| 3-17 | 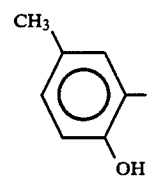 | |
| 3-18 | 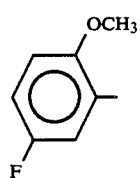 | |
TABLE I-continued
| | | |
|---|---|---|
| 3-19 | 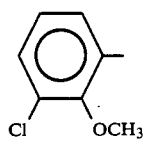 | |
| 3-20 | 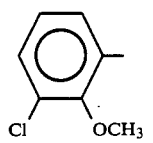 | |
| 3-21 | 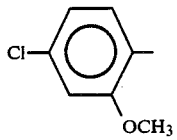 | |
| 3-22 | 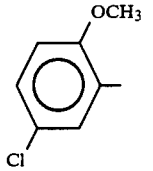 | |
| 3-23 | 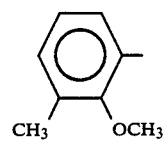 | |
| 3-24 | 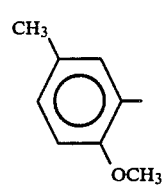 | |
| 3-25 | 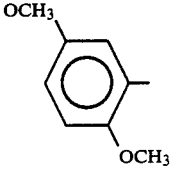 | |
| 3-26 | 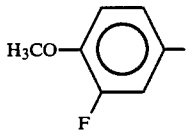 | |
| 3-27 | 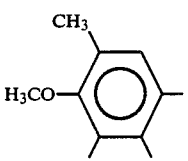 | |

TABLE I-continued
| | | |
|---|---|---|
| 3-28 | 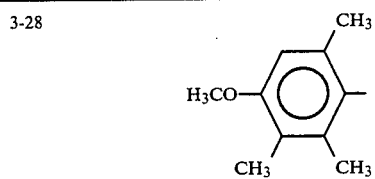 | |
| 3-29 | 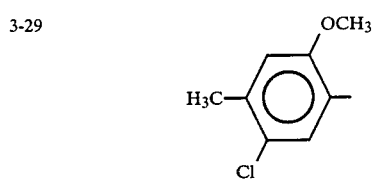 | |
| 3-30 | 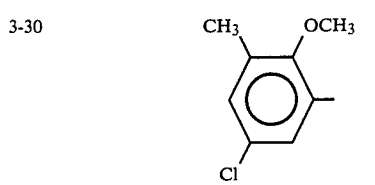 | |
| 3-31 | 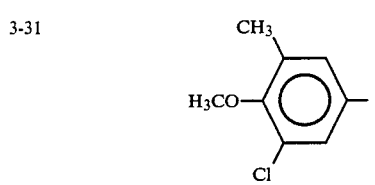 | |
| 3-32 | 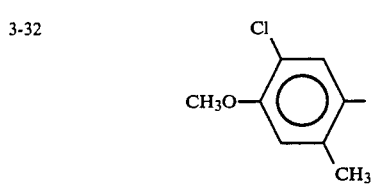 | |
| 3-33 | 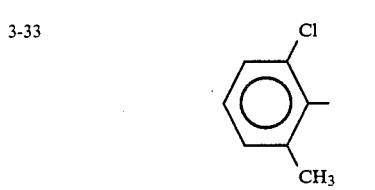 | |
| 3-34 | 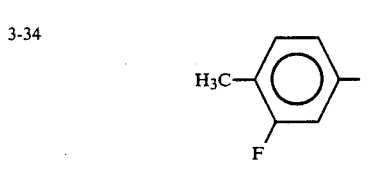 | |
| 3-35 | 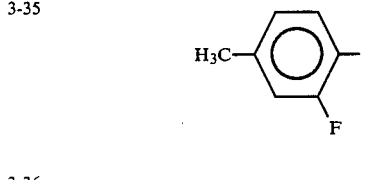 | |
| 3-36 | 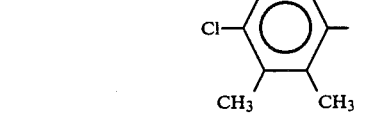 | |
TABLE I-continued
| | | |
|---|---|---|
| 3-37 | 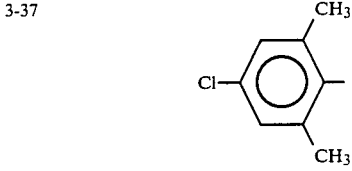 | |
| 3-38 | 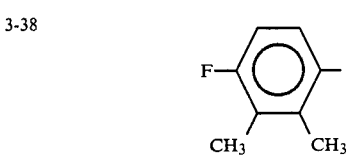 | |
| 3-39 | 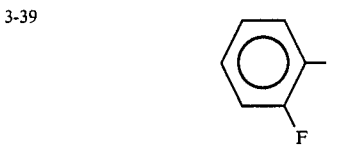 | |
| 3-40 | 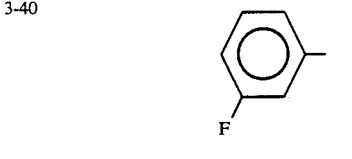 | |
| 4-1 | 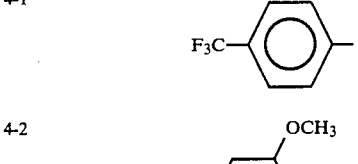 | |
| 4-2 | 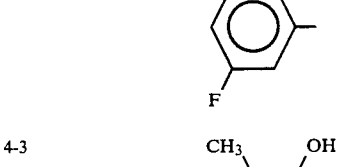 | |
| 4-3 | 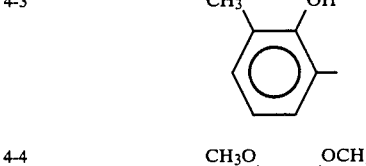 | |
| 4-4 | 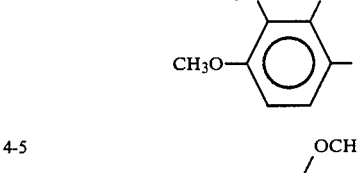 | |
| 4-5 | 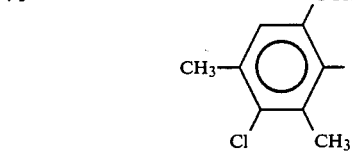 | |
| 4-6 | 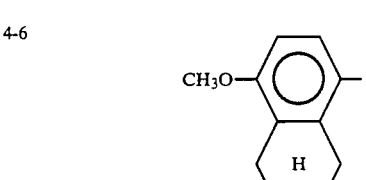 | |

TABLE I-continued

| No. | Structure |
|---|---|
| 4-7 | 5,6,7,8-tetrahydronaphthalen-1-ol (HO- substituted tetrahydronaphthalene) |
| 4-8 | 5,6,7,8-tetrahydro-N,N-dimethylnaphthalen-1-amine ((CH₃)₂N- substituted tetrahydronaphthalene) |
| 4-9 | 1-methoxynaphthalene (CH₃O- substituted naphthalene) |

TABLE II (Compounds represented by the general formula (I)

$$R^1-CO-CH(R^2)-CH(R^3)-(CH_2)_n-NR_aR_b$$

wherein $R^1$, $R^2$, $R^3$, n and $-NR_aR_b$ are defined as stated in Table II below.)

| Compound No. | $R^1$ | $R^2$ | $R^3$ | n | $-NR_aR_b$ |
|---|---|---|---|---|---|
| 4-10 | 2,3-dimethylphenyl | CH₃ | H | 0 | piperidino |
| 4-11 | 2,3,4-trimethoxyphenyl | CH₃ | H | 0 | piperidino |
| 4-12 | 3-methoxy-4,6-dimethylphenyl (CH₃O-, CH₃-, CH₃-) | CH₃ | H | 0 | piperidino |
| 4-13 | 2-methoxy-3,5-dimethylphenyl (CH₃, OCH₃, CH₃) | CH₃ | H | 0 | piperidino |
| 4-14 | 2,3-dimethylphenyl | C₂H₅ | H | 0 | pyrrolidino |
| 4-15 | 3,4-dimethylphenyl | C₂H₅ | H | 0 | pyrrolidino |
| 4-16 | 3-methoxy-4,6-dimethylphenyl | C₂H₅ | H | 0 | pyrrolidino |
| 4-17 | 2-methoxy-3,5-dimethylphenyl (CH₃, OCH₃, CH₃) | C₂H₅ | H | 0 | pyrrolidino |
| 4-18 | 3,4-dimethylphenyl | H | CH₃ | 0 | pyrrolidino |
| 4-19 | 2-methoxy-3,5-dimethylphenyl (CH₃, OCH₃, CH₃) | H | CH₃ | 0 | pyrrolidino |
| 4-20 | 2-methoxy-3,5-dimethylphenyl (CH₃, H₃CO-, CH₃) | H | CH₃ | 0 | pyrrolidino |

TABLE II-continued (Compounds represented by the general formula (I)

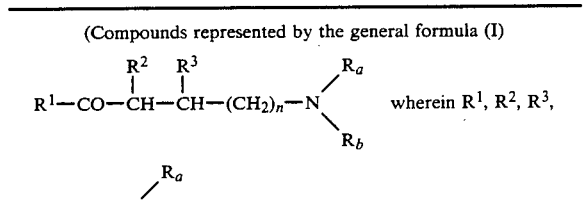

wherein $R^1$, $R^2$, $R^3$, n and $-N\begin{matrix}R_a\\R_b\end{matrix}$ are defined as stated in Table II below.)

| Compound No. | $R^1$ | $R^2$ | $R^3$ | n | $-N\begin{matrix}R_a\\R_b\end{matrix}$ |
|---|---|---|---|---|---|
| 2-1 | 5-methoxy-tetrahydronaphthyl (CH₃O-) | CH₃ | H | 0 | pyrrolidinyl |
| 2-2 | 5-ethoxy-tetrahydronaphthyl (C₂H₅O-) | CH₃ | H | 0 | pyrrolidinyl |
| 2-3 | 5-propoxy-tetrahydronaphthyl (C₃H₇O-) | CH₃ | H | 0 | pyrrolidinyl |
| 2-4 | 5-methoxy-tetrahydronaphthyl (CH₃O-) | CH₃ | H | 0 | piperidinyl |
| 2-5 | 5-propoxy-tetrahydronaphthyl (C₃H₇O-) | CH₃ | H | 0 | piperidinyl |
| 2-6 | 5-chloro-tetrahydronaphthyl (Cl-) | CH₃ | H | 0 | pyrrolidinyl |

TABLE II-continued (Compounds represented by the general formula (I)

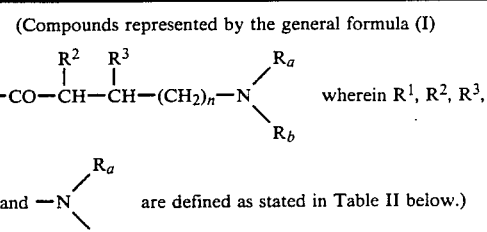

wherein $R^1$, $R^2$, $R^3$, n and $-N\begin{matrix}R_a\\R_b\end{matrix}$ are defined as stated in Table II below.)

| Compound No. | $R^1$ | $R^2$ | $R^3$ | n | $-N\begin{matrix}R_a\\R_b\end{matrix}$ |
|---|---|---|---|---|---|
| 2-7 | 5-chloro-tetrahydronaphthyl (Cl-) | CH₃ | H | 0 | piperidinyl |
| 2-8 | 5-methyl-tetrahydronaphthyl (CH₃-) | CH₃ | H | 0 | pyrrolidinyl |
| 2-9 | tetrahydronaphthyl | CH₃ | H | 0 | pyrrolidinyl |
| 2-10 | 5-methoxy-tetrahydronaphthyl (CH₃O-) | CH₃ | H | 0 | $-N(C_2H_5)_2$ |
| 2-11 | 5-methoxy-tetrahydronaphthyl (CH₃O-) | C₂H₅ | H | 0 | pyrrolidinyl |
| 2-16 | 5-methoxy-tetrahydronaphthyl (CH₃O-) | H | H | 0 | pyrrolidinyl |

TABLE II-continued (Compounds represented by the general formula (I))

$$R^1-CO-\underset{R^2}{\overset{}{C}H}-\underset{R^3}{\overset{}{C}H}-(CH_2)_n-N\underset{R_b}{\overset{R_a}{\diagup}}$$

wherein $R^1$, $R^2$, $R^3$, n and $-N\underset{R_b}{\overset{R_a}{\diagup}}$ are defined as stated in Table II below.

| Compound No. | $R^1$ | $R^2$ | $R^3$ | n | $-N\underset{R_b}{\overset{R_a}{\diagup}}$ |
|---|---|---|---|---|---|
| 2-17 | 6-CH₃O-5,6,7,8-tetrahydronaphthyl | H | H | 1 | pyrrolidinyl |
| 2-18 | 6-CH₃O-5,6,7,8-tetrahydronaphthyl | H | CH₃ | 0 | pyrrolidinyl |
| 2-12 | 6-OCH₃-5,6,7,8-tetrahydronaphthyl | CH₃ | H | 0 | pyrrolidinyl |
| 2-13 | 6-OCH₃-5,6,7,8-tetrahydronaphthyl | CH₃ | H | 0 | piperidinyl |
| 2-14 | 6-Cl-5,6,7,8-tetrahydronaphthyl | CH₃ | H | 0 | pyrrolidinyl |
| 2-15 | 6-CH₃-5,6,7,8-tetrahydronaphthyl | CH₃ | H | 0 | pyrrolidinyl |

TABLE II-2

(Compound represented by the general formula (II))

$$R_4-\text{Ph}-COCHCH_2-N\underset{R_e'}{\overset{R_d}{\diagup}}$$
with $R_c$ on the CH wherein $R_4$, $R_c$ and $-N\underset{R_e'}{\overset{R_d}{\diagup}}$ are defined as stated in Table II-2 below.

| Compound No. | $R_4$ | $R_c$ | $-N\underset{R_e'}{\overset{R_d}{\diagup}}$ | Remarks |
|---|---|---|---|---|
| 4-1 | $-CF_3$ | $-CH_3$ | pyrrolidinyl | |
| 4-1-l | $-CF_3$ | $-CH_3$ | pyrrolidinyl | l-isomer |
| 4-1-d | $-CF_3$ | $-CH_3$ | pyrrolidinyl | d-isomer |
| 5-1 | $-CF_3$ | $-CH_3$ | piperidinyl | |
| 5-2 | $-CF_3$ | $-CH_2CH_3$ | piperidinyl | |
| 5-3 | $-CF_3$ | $-CH_2CH_3$ | $-N(CH_2CH_3)_2$ | |

Among the compounds of this invention of which the typical examples were shown above, the preferred compounds are those of $R^1$ is a group selected from the groups of the formulae phenyl substituted with $R^4$; phenyl substituted with $R^6$; phenyl substituted with $R^7$, $R^8$; phenyl substituted with $R^9$, $R^{10}$; phenyl substituted with $R^9$, $R^{11}$, $R^{12}$; phenyl substituted with $R^9$, $R^{13}$, $R^{14}$, -continued

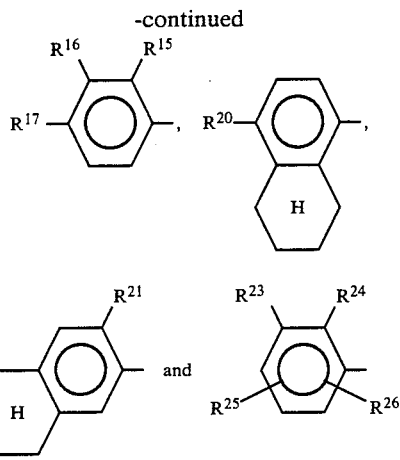

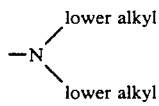

(in which $R^6$ is a halogen atom, $R^7$, $R^8$, $R^{11}$, $R^{14}$, $R^{15}$ and $R^{16}$ each are lower alkyl groups, $R^{10}$ and $R^{13}$ each are lower alkyl groups or lower alkoxyl groups, $R^{17}$ is a hydrogen atom, $R^{20}$ is a hydrogen atom, $$-N\begin{matrix}\text{lower alkyl}\\\text{lower alkyl}\end{matrix}$$

or a lower alkyl group, $R^{21}$ is a lower alkoxyl group, $R^4$, $R^9$, $R^{12}$, $R^{23}$, $R^{24}$, $R^{25}$ and $R^{26}$ each are the same as described above).

The more preferred compounds are those of which $R^1$ is a group selected from the groups of the formulae

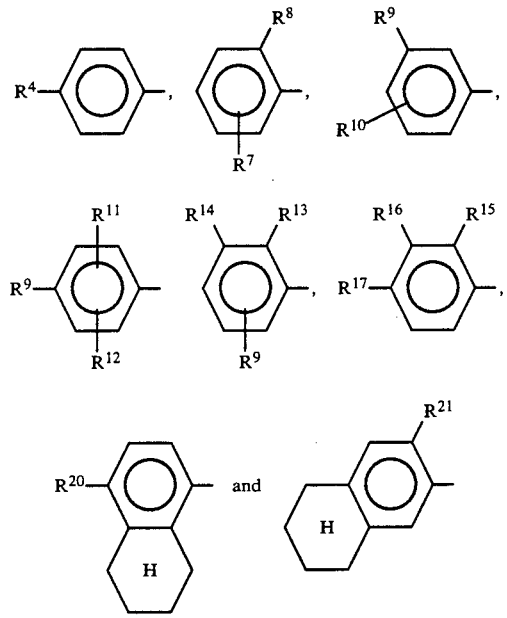

(in which $R^7$, $R^8$, $R^{10}$, $R^{11}$, $R^{14}$, $R^{15}$ and $R^{16}$ each are lower alkyl groups, $R^{12}$ is a halogen atom, $R^{13}$ and $R^{21}$ each are lower alkoxyl groups, $R^{17}$ is a hydrogen atom, $R^{20}$ is a hydrogen atom or a lower alkoxyl group, $R^4$ and $R^9$ each are the same meanings as described above).

The especially preferred compounds are those of which $R^1$ is a group selected from the groups

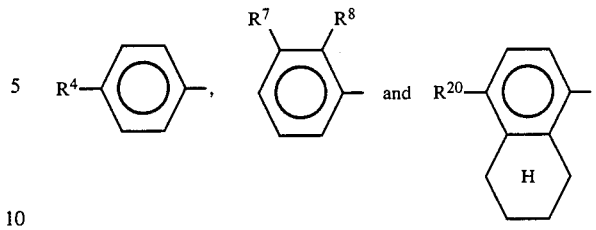

(in which $R^7$ and $R^8$ each are lower alkyl groups and $R^{20}$ is a lower alkoxyl group, and $R^4$ is the same meanings as described above.)

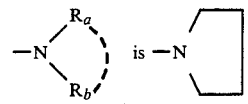

$R^2$ is a lower alkyl group, and $R^3$ is a hydrogen atom and n is 0.

The preferred compounds, when indicated by the numbers (Compound No.) shown in the above tables, are as follows: preferred compounds are, for example, 1-1, 1-3, 1-13, 1-17, 1-20, 1-21, 2-1, 2-3, 2-4, 2-6, 2-9, 2-10, 2-11, 2-12, 2-16, 2-17, 2-18, 3-25, 3-31, 3-34, 3-36, 3-38, 3-40, 4-1, 4-5, 4-8, 4-10, 4-15 and 4-18, etc.. More preferred compounds are, for example, 1-3, 1-13, 1-17, 2-1, 2-3, 2-4, 2-9, 2-10, 2-11, 2-12, 2-16, 2-17, 2-18, 3-31, 3-34, 4-1, 4-5 and 4-10, etc. Especially preferred compounds are, for example, 1-13, 2-1, 2-11 and 4-1, etc.

The compounds of this invention can be obtained by reacting an amine represented by the general formula:

 (b)

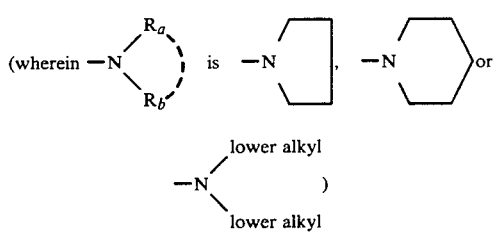

with e,crc/1/ a compound represented by the general formula:

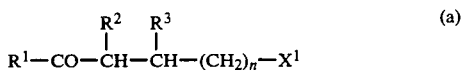 (a)

wherein $X^1$ is halogen atom, n is 0 or 1, and $R^1$, $R^2$ and $R^3$ are as defined above), ② formaldehyde or a compound represented by the general formula:

 (c)

(wherein R$^1$ and R$^2$ are as defined above), or ③ a compound represented by the general formula:

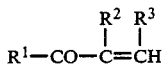

(wherein R$^1$, R$^2$ and R$^3$ are as defined above).

The reaction is preferably carried out at a temperature of 0°–200° C. for a period of about 0.5–48 hours.

The process for preparing the compounds of this invention is illustrated more particularly below.

(1) In case of using the compound ①, the process comprises condensing, in an inert solvent, a compound represented by the general formula:

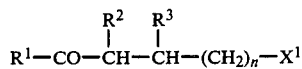

(wherein X$^1$ is halogen atom, n is 0 or 1, and R$^1$, R$^2$ and R$^3$ are as defined above) and an amine represented by the general formula:

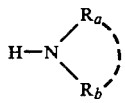

(wherein

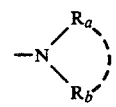

is as defined above).

This condensation reaction is preferably carried out in an inert solvent, for example, dimethylformamide, a ketone such as acetone, etc., or an alcohol such as ethanol, by adding a base catalyst such as anhydrous potassium carbonate and potassium iodide, at a temperature of from 0° to 200° C., preferably from 10° C. to near the boiling point of the solvent, for a period of about 0.5 to 48 hours In the reaction, an amine of formula (b) or its salt is used in an amount of 0.5 equivalent or more, preferably 1 to 10 equivalents, to one equivalent of the halogen compound of the formula (a).

A typical example of the compounds of the formula (a) is 1-(4-methoxy-5,6,7,8-tetrahydro-1-naphthyl)-4-chloro-1-butane.

(2) The process using the compound ② is suited for obtaining the compounds of the formula (I) in which R$^3$ is a hydrogen atom and n is 0, that is, new aminoketone derivatives represented by the general formula:

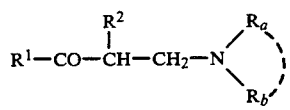

(wherein R$^1$, R$^2$ and

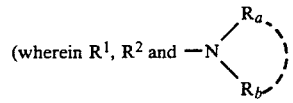

are as defined above.) that is to say the compound of the formula:

(wherein R$^1$ and R$^2$ are as defined above), with formaldehyde and an amine represented by the general formula (b):

(wherein

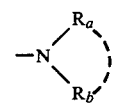

is as defined above).

As for the ratio of the compound of the formula (c), formaldehyde and the compound of the formula (b) used in the reaction, formaldehyde is used in a ratio of usually 0.5 equivalent or more, preferably 1 to 10 equivalents, more preferably 1.5 to 6 equivalents, to one equivalent of the compound of the formula (c), and the amine or its salt of the formula (b) is used in a ratio of usually 0.5 to 10 equivalents, preferably 1 to 3 equivalents to one equivalent of the compound of the formula (c). Formaldehyde can be used as in the form of formalin or paraformadehyde. The reaction can be carried out under the Mannich reaction conditions, preferably in the presence of a catalytic amount of an acid, especially hydrochloric acid. Although the reaction can be accomplished without using solvent, it is preferred to use an alcohol solvent such as propanol, isopropanol, butanol, isobutanol, etc., a ketone solvent such as acetone, methyl ethyl ketone, etc., an ester solvent such as ethyl acetate or the like.

The reaction is preferably carried out at a temperature from 0° to 200° C., preferably from 10° C. to near the boiling point of the solvent used, for a period of about 0.5 to 48 hours.

This method is also applicable to the preparation of the compounds of the general formula (II).

Listed below are the examples of the compounds of the formula (c) used in the reaction: 1-(2,5-dimethyl-4-methoxyphenyl)-1-propanone, 1-(4,5-dimethyl-2-methoxyphenyl)-1-propanone, 1-(3,5-dimethyl-2-methoxyphenyl)-1-propanone, 1-(2,6-dimethyl-4-methoxyphenyl)-1-propanone, 1-(3,5-dimethyl-4-methoxyphenyl)-1-propanone, 1-(3,4-dimethyl-2-methoxyphenyl)-1-propanone, 1-(3,6-dimethyl-2-methoxyphenyl)-1-propanone, 1-(4,6-dimethyl-2-methoxyphenyl)-1-propanone, 1-(4,5-dimethyl-4-hydroxyphenyl)-1-propanone, 1-(3,4-dimethyl-2-hydroxyphenyl)-1-propanone, 1-(3,6-dimethyl-2-hydroxyphenyl)-1-propanone, 1-(3,4-dimethylphenyl)-

1-propanone, 1-(2,3-dimethylphenyl)-1-propanone, 1-(2,4-dimethylphenyl)-1-propanone, 1-(3,5-dimethylphenyl)-1-propanone, 1-(2,5-dimethylphenyl)-1-propanone, 1-(2-methyl-5-isopropylphenyl)-1-propanone, 1-(2,4,5-trimethylphenyl)-1-propanone, 1-(2,3,4-trimethylphenyl)-1-propanone, 1-(3,4,5-trimethylphenyl)-1-propanone, 1-(2,3,5,6-tetramethylphenyl)-1-propanone, 1-(2-methylphenyl)-1-propanone, 1-(3-methylphenyl)-1-propanone, 1-(3-bromophenyl)-1-propanone, 1-(3-(2-cyclohexenyl)phenyl)-1-propanone, 1-(2-$\alpha,\alpha,\alpha$-trifluoromethylphenyl)-1-propanone, 1-(3-$\alpha,\alpha,\alpha$-trifluoromethylphenyl)-1-propanone, 1-(2-isopropylphenyl)-1-propanone, 1-(2-ethylphenyl)-1-propanone, 1-(2-vinylphenyl)-1-propanone, 1-(3-vinylphenyl)-1-propanone, 1-(2-biphenyl)-1-propanone, 1-(3-biphenyl)-1-propanone, 1-(2-hydroxy-5-methylphenyl)-1-propanone, 1-(3-fluoro-6-methoxyphenyl)-1-propanone, 1-(3-chloro-2-methoxyphenyl)-1-propanone, 1-(4-chloro-2-methoxyphenyl)-1-propanone, 1-(3-chloro-6-methoxyphenyl)-1-propanone, 1-(2-methoxy-3-methylphenyl)-1-propanone, 1-(2-methoxy-5-methylphenyl)-1-propanone, 1-(2,5-dimethoxyphenyl)-1-propanone, 1-(3-fluoro-4-methoxyphenyl)-1-propanone, 1-(4-methoxy-2-methylphenyl)-1-propanone, 1-(4-methoxy-2,3,5-trimethylphenyl)-1-propanone, 1-(4-methoxy-2,3,6-trimethylphenyl)-1-propanone, 1-(3-chloro-6-methoxy-4-methylphenyl)-1-propanone, 1-(3-chloro-6-methoxy-5-methylphenyl)-1-propanone, 1-(3-chloro-4-methoxy-5-methylphenyl)-1-propanone, 1-(3-chloro-4-methoxy-6-methylphenyl)-1-propanone, 1-(2-chloro-6-methylphenyl)-1-propanone, 1-(3-fluoro-4-methylphenyl)-1-propanone, 1-(2-fluoro-4-methylphenyl)-1-propanone, 1-(4-chloro-2,3-dimethylphenyl)-1-propanone, 1-(4-chloro-2,6-dimethylphenyl)-1-propanone, 1-(4-fluoro-2,3-dimethylphenyl)-1-propanone, 1-(2-fluorophenyl)-1-propanone, 1-(3-fluorophenyl)-1-propanone, 1-(4-$\alpha,\alpha,\alpha$-trifluoromethylphenyl)-1-propanone, 1-(3-fluoro-6-methoxyphenyl)-1-propanone, 1-(2,3,4-trimethoxyphenyl)-1-propanone, 1-(2-methoxy-5-chloro-4,6-dimethylphenyl)-1-propanone, 1-(7-methoxy-4-indanyl)-1-propanone, 1-(4-hydroxy-5,6,7,8-tetrahydro-1-naphthyl)-1-propanone, 1-(4-dimethylamino-5,6,7,8-tetrahydro-1-naphthyl)-1-propoanone, 1-(2,3-dimethylphenyl)-1-propanone, 1-(4-methoxy-2,5-dimethylphenyl)-1-propanone and 1-(2-methoxy-3,5-dimethylphenyl)-1-propanone, etc.

(3) The process using the compound ③ is suited for obtaining the compounds of the formula (I) in which n is 0, that is, the compounds represented by the following general formula:

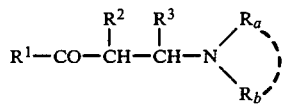

(wherein $R^1$ and

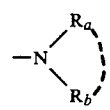

are as defined above).

The compounds of the above formula can be readily obtained by reacting an amine of formula (b) with a compound represented by the following general formula:

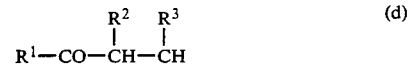

(wherein $R^1$, $R^2$ and $R^3$ are as defined above) under the Michael reaction conditions.

The ratio of the compound of the formula (d) and an amine used in the reaction is usually 0.5 equivalent or more, preferably 1 to 10 equivalents of amine to one equivalent of the compound of the formula (d).

Although the reaction can be accomplished without solvent, it is better to use a solvent Alcohols such as methanol and ethanol can be used as solvent. For obtaining a desirable result, the reaction is carried out at a temperature from 0° to 200° C., preferably from 0° C. to near the boiling point of the solvent used, for a period of 0.5 to 48 hours Listed below are the example of the compounds of the formula (d) used in the reaction 1-(2,4-dimethylphenyl)-2-butene-1-one, 1-(2-methoxy-3,5-dimethylphenyl)-2-butene-1-one, 1-(4-methoxy-2,5-dimethylphenyl)-2-butene-1-one, and 1-(4-methoxy-5,6,7,8-tetrahydro-1-naphthyl)-2-butene-1-one, etc.

The compounds of the formulae (a), (c) and (d) used as starting compound in this reaction can be obtained usually by reacting a compound represented by the general formula:

$R^1\text{-H}$ (e)

(wherein $R^1$ is as defined above) and a compound represented by the general formula:

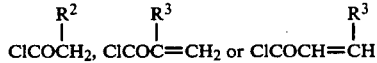

(wherein $R^2$ and $R^3$ are as defined above).

The compounds of the formula (c) can be obtained by the following method, that is, the Grinard reagent or the lithium reagent is prepared by reacting magnesium or lithuim with a halogenated benzene derivative or a halogenated tetrahydronaphthalene derivative. These reagents are reacted with the corresponding aldehydes to give alcohols. The alcohols are oxidized with chromic acid anhydride or the like.

In addition, when the substituent on the benzene or tetrahydronaphthyl group in the general formula (I) is a halogen atom such as chlorine atom, the desired compound can be obtained by the Sandmeyer or Schiemann reaction of the amine derivatives such as

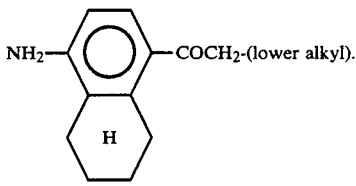

The compounds of this invention represented by the general formula (I) are purified and isolated from the reaction solution in the usual way. Such compounds can be obtained in the form of free bases or these salts by properly selecting the reaction conditions or the treating process.

Free bases, if desired, can be transformed into acid addition salts by a conventional method. Such acid addition salts include inorganic acid salts such as hydrochloride, hydrobromide, sulfate, phosphate, etc., and organic acid salts such as formate, acetate, citrate, maleate, fumarate, tartrate, lactate, methanesulfonate, etc.

It is to be noted that some of the compounds of this invention have one asymmetric carbon atom in the molecule and therefore there exist theoretically two optical isomers, so that the present invention comprehends the racemates and optical isomers of these compounds. Optically active compounds can be obtained from the racemates Optical resolutions of, for instance, the compound of No. 4-1 can be accomplished in the following way That is, the racemate of the compound is reacted with an optically active acetylphenylglycine or an optically active malic acid in an appropriate solvent to form two kinds of diastereomeric salts The resulting solution is concentrated, cooled, or to the solution was added the solvent which can decrease the solubility of the salt to deposit crystals of a slightly solubble diastereomeric salt. The crystals are separated from the liquid, and the resulting salt from reacting optically active compound of No. 4-1 with the optically active acetylphenylglycine or the optically active malic acid are decomposed by an aqueous alkali solution, and the optically active isomer of the compound of No. 4-1 can be isolated.

Though the solvent used in this process is not limited, so long as a solvent in which both of racemate of the compound of No. 4-1 and optically active acetylphenylglycine or optically active malic acid can be dissolved to form diastereomeric salts as well as in which both of the slightly soluble and easily soluble diastereomeric salts can be dissolved at a temperature of the range from room temperature to boiling point of the solvent and then the slightly soluble diastereomeric salt is deposited as crystals by concentration, cooling or addition of the other solvent. The preferred solvents are ketones such as acetone, methyl ethyl ketone, methyl isobutyl ketone; alcohols such as methanol, ethanol, propanol, isopropanol; and alkyl aliphatic carboxylate, for example $C_1$–$C_4$ alkyl acetate such as methyl acetate, ethyl acetate, butyl acetate. Particularly ethyl acetate and isopropanol are preferable.

The proportion of racemate of the compound of No. 4-1 to optically active acetylphenylglycine or optically active malic acid to be used is about 0.5 to 1.5 equivalents, preferably about one equivalent, of the latter per equivalent of the former.

In this case, if D-acetylphenylglycine is used, the crystalline salt of d-isomer of the compound of No. 4-1 is deposited as the slightly soluble diastereomeric salt, while if L-acetylphenylglycine or D-malic acid is used, crystalline salt of l-isomer of the compound of No. 4-1 is deposited.

Though the temperature at which the racemate of the compound of No. 4-1 is reacted with an optically active acetylphenylglycine or optically active malic acid is not limited, preferred is a temperature of the range from room temperature to the boiling point of the solvent. Also, though the proportion of the amount of the solvent to be used to the amount of the diastereomeric salt may be in the wide range of from about 0.1 time (V/W) to about 10 times (V/W), preferred is about 0.1 time (V/W) to about 4 times (V/W).

The crystal depositing time is about 1 - 150 hours, preferably about 1 - 60 hours, more preferably about 10 - 50 hours.

The crystal depositing temperature may be below the boiling point of the solvent used, and preferred is a temperature in the range of 0° to 70° C., particularly 0° to 50° C. The solvents which decrease the solubility include tetrahydrofuran, ethyl acetate, ethers and the like Decomposition of the obtained optically active diastereomeric salt into an optically active compound of No. 4-1 and an optically active acetylphenylglycine or optically active malic acid can be carried out in water in the presence of an alkali such as ammonia, sodium bicarbonate, potassium bicarbonate, diluted aqueous sodium hydroxide solution or the like at 0° to 50° C., preferablyly at 0° to 30° C. In this case, the amount of alkali may be an equivalent or more per equivalent of the diastereomeric salt.

Isolation of the optically active compound of No. 4-1 from the decomposition solution can be carried out by extracting it with a nonhydrophylic solvent such as an ether, ethyl acetate, methylene chloride or the like at 0° C. to 40° C., and then distilling off the solvent.

Furthermore, when the decomposition of the salt is carried out in the co-existance of an aqueous alkali solution and the above-mentioned organic solvent, the decomposition and extraction of the optically active compound of No. 4-1 can be accomplished simultaneously.

In use of the obtained compounds of this invention as a central muscle relaxant, the compounds can be administered either orally or parenterally. The effective dose varies depending on the condition and age of the patient being treated and the method of administration, but it is usually 0.1–20 mg/kg/day.

The compounds of this invention are administered in the form of pharmaceutical preparations composed by mixing the compounds with an appropriate pharmaceutical carrier. Such pharmaceutical preparations include tablet, granules, fine grains, powder, capsule, injection, suppository and the like.

EFFECT

The pharmaceutical activity of the compounds of this invention is described below.

1. Spinal reflex (flexor reflex) inhibitory action

Animals (male rats; Wistar strain) were anesthetized with urethane and $\alpha$-chloralose, and their tibial nerve was dissected, and stimulated (0.1 msec, 0.1 Hz, Supramaximum stimulation) by the stimulator (Model MSE-3; Nihon Koden). The evoked electromyogram recorded through a needle electrode inserted into the ipsilateral muscle tibialis was amplified and displayed on a cathoderay oscilloscope. The amplitude of this evoked electromyogram was recorded on a pen recorder through a peak holder. The activity of the compounds was expressed by flexor reflex inhibition rate. That is, the flexor reflex inhibition rate was calculated from the following equation (A):

$$\text{Inhibition rate} = \frac{A - B}{A} \times 100\ (\%) \qquad (A)$$

wherein A is the average amplitude of the electromyogram in the period of 10 minutes before the administration of the test compound, and B is the average amplitude of the electromyogram in the period of 30 minutes after the intravenous (i.v.) administration of 5 mg/kg of the test compound dissolved in a physiological saline solution.

The results are shown in Table III below.

TABLE III

| Compound No. | Inhibition rate (%) | Compound No. | Inhibition rate (%) |
|---|---|---|---|
| 1-1 | 57.3 | 3-23 | 33.1 |
| 1-3 | 58.2 | 3-29 | 42.4 |
| 1-4 | 41.4 | 3-31 | 45.6 |
| 1-6 | 38.5 | 3-33 | 34.7 |
| 1-7 | 42.4 | 3.34 | 50.0 |
| 1-8 | 49.7 | 3.35 | 37.3 |
| 1-12 | 39.4 | 3-36 | 48.8 |
| 1-13 | 55.5 | 3-38 | 38.4 |
| 1-14 | 57.2 | 3-40 | 41.5 |
| 1-15 | 41.5 | 4-1 | 40.3 |
| 1-16 | 45.0 | 4-1-1 | 34.3 |
| 1-18 | 48.1 | 4-5 | 44.4 |
| 1-19 | 38.5 | 4-10 | 47.8 |
| 1-20 | 41.2 | 4-12 | 41.9 |
| 1-21 | 52.8 | 4-14 | 56.8 |
| 3-5 | 51.0 | 4-15 | 32.0 |
| 3-6 | 33.7 | 4-18 | 32.4 |
| 3-13 | 44.6 | 1-49 | 46.2 |
| 3-17 | 43.7 | 4-19 | 55.0 |
| 3-18 | 40.0 | 2-1 | 53.6 |
| 3-21 | 33.1 | 2-4 | 40.4 |
| 3-22 | 41.4 | 2-11 | 50.0 |
|  |  | 2-12 | 50.8 |

2. Action to ischemic decerebrate riqidity of rat

The effects on the ischemic decerebrate rigidity was investigated by using Fukuda et al method (H. Fukuda, T. Ito, S. Hashimoto and Y. Kudo: Japan. J. Pharmacol., 24, 810 (1974)). The rigidity is due to hyperactivity of α-motoneurones. The rigid animals provide a good experimental model for some type of spasticity in man.

METHOD:

A tracheal cannula was inserted in each of male Wistar rat under ether anesthesia. Both of common carotid arteries were ligated and the basilar artery was cauterized with a bipolar coagulato to block the blood circulation and to prepare a rigidity sample. The rigidity was recorded as described below. A rat was fixed on its back on a fixing stand and its forepaws were allowed to grisp an end of a celluloid plate provided with strain gauges on both sides thereof. A change of the resistance observed when the celluloid plate was forced up by the rigidity of the forepaws was recorded as a tension through a bridge circuit on a self-balancing recorder. A rigidity inhibition rate was calculated according to the following equation:

$$\text{Rigidity inhibition rate} = \frac{C - D}{C} \times 100 \, (\%)$$

when C represents an average tension (g) for 10 minutes at peak period before the administration of a test compound and D represents an average for 10 minutes at peak period tension (g) recorded after the intravenous administration 3.5 mg/kg of a test compound.

The results are shown in Table IV.

TABLE IV

| Compound No. | Inhibition rate (%) |
|---|---|
| 2-1 | 46.1 |
| 2-11 | 53.9 |
| 4-1 | 23.6 |
| 1-13 | 25.8 |

The similar test was conducted by using the compound No. 4-1-1 which was administered orally to the mice. The rigidity inhibition rate was expressed in terms of percent to the tension before the administration as follows:

$$(100 - \frac{\text{tension 30 min. after administration}}{\text{tension before administration}} \times 100) \, (\%)$$

The test compound was dissolved in distilled water and 100 mg/kg thereof was given to the mice through a previously inserted gastro-catheter.

The thus determined rigidity inhibition rate of the intragastorically administered compound No. 4-1-1 was 51.3%.

3. Acute toxicity $LD_{50}$ (mg/kg) of the each test compound given to mice intravenously was determined.

The results are shown below.

TABLE V

| Compound No. | $LD_{50}$ (Mice; i.v.) mg/kg | Compound No. | $LD_{50}$ (Mice; i.v.) mg/kg |
|---|---|---|---|
| 1-1 | 21.5 | 3-5 | 30.0 |
| 1-3 | 23.9 | 3-6 | 30–40 |
| 1-4 | 20–30 | 3-13 | 26.0 |
| 1-6 | 2–30 | 3-17 | 38.7 |
| 1-7 | 20–30 | 3-21 | 20–30 |
| 1-8 | 20–30 | 3-22 | 20–30 |
| 1-12 | 20–30 | 3-23 | 30–40 |
| 1-13 | 10–20 | 3-29 | 20–30 |
| 1-14 | 20–30 | 3-31 | 30–40 |
| 1-15 | 10–20 | 3-36 | 30–50 |
| 1-16 | 20–30 | 3-38 | 30–40 |
| 1-18 | 20–30 | 4-1 | 61.1 |
| 1-19 | 20–30 | 2-1 | 38.1 |
| 1-20 | 20–30 | 2-4 | 37.8 |
| 1-21 | 10–20 | 2-11 | 35.4 |

$LD_{50}$ of the compounds No. 4-1-1 was 107 mg/kg and that of the compound No. 4-1-d was 63 mg/kg. The compound No. 4-1, which was tested for the reference's sake, showed $LD_{50}$ of 83 mg/kg. Also, the compound No. 4-1-1 showed an acute toxicity ($LD_{50}$) of 620 mg/kg in intragastorical administration to mice.

As viewed above, the compounds of this invention have an excellent inhibitory action on spinal reflex (flexor reflex) and are also low in toxicity. Further, the compounds of this invention show a depression activity on the decerebrate rigidity which is regarded as one of the good experimental models of spastic palsy, and are longacting. They also have an anticonvulsive action. Thus, it is expected that the compounds of this invention would be of use ① as a central muscle relaxant having an excellent therapeutical effect on spastic palsy resulting from cerebral vascular trouble, cerebral paralysis, spondylosis, etc., and on muscular hypertonia accompanied with various diseases, and ② for the treatment of spastic paralysis or the improvement of hypertonia of muscles in a homoisothermic animal having spastic paralysis or hypertonia of muscles.

The process for producing the compounds of this invention will now be described with reference to Examples.

EXAMPLE 1

1-(4-Methoxy-5,6,7,8-tetrahydro-1-naphthyl)-2-ethyl-3-pyrrolidino-1-propanone (Compd. Nos. 2-11) hydrochloride.

A mixture of 1-(4-methoxy-5,6,7,8-tetrahydro-1-naphthyl)-1-butanone (2.50g), paraformaldehyde (0.42g), pyrrolidine hydrochloride (1.51g), and hydrochloric acid (0.2 ml) in isopropyl alcohol (7 ml) was refluxed for 15 hrs. The reaction mixture was evaporated in vacuo to give the residue. The residue was partitioned into water and ethyl ether. The aqueous layer, was extracted, neutralized with ammonia water, and then extracted with ethyl ether. The organic layer was dried over anhydrous magnesium sulfate. The mixture was filtered and the filtrate was evaporated in vacuo to give 1-(4-methoxy-5,6,7,8-tetrahydro-1-naphthyl)-2-ethyl-3-pyrrolidino-1-propanone (2.13 g, Yield: 62.8 %) as an oil.

IR $\nu_{max}$

NMR δ (CDCl₃, TMS): 0.90 (t, 3H, J=7.0 Hz; CH₂CH₃), 1.2–2.1

(m, 10H, 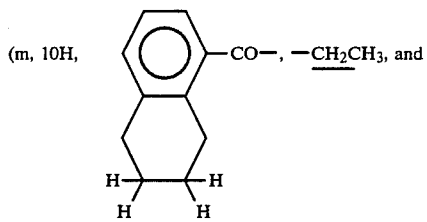 —CO—, —CH₂CH₃, and

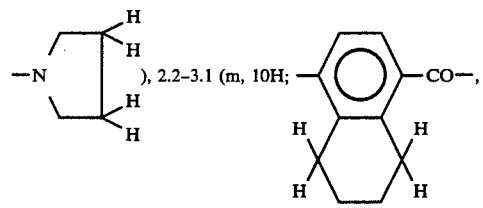), 2.2–3.1 (m, 10H; 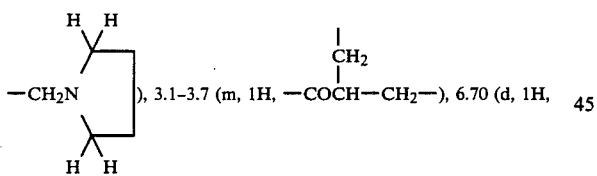 —CO—,

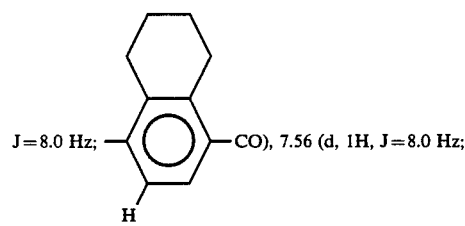), 3.1–3.7 (m, 1H, —COCH—CH₂—), 6.70 (d, 1H,

J=8.0 Hz; 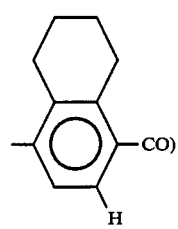 —CO), 7.56 (d, 1H, J=8.0 Hz;

TABLE VI-1

($R^1$ substituents of compounds represented by
the formula $R^1-\overset{O}{\underset{\|}{C}}-\overset{CH_3}{\underset{|}{CH_2}}$ which are
used as one of the starting materials for
the compounds represented by the general
formula (I) listed in Table I.)

| Compound No. | $R^1$ |
|---|---|
| 1-1 | 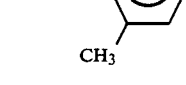 |
| 1-2 | 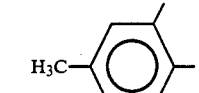 |
| 1-3 | 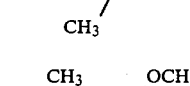 |
| 1-4 |  |
| 1-5 | 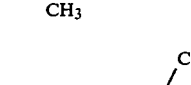 |
| 1-6 | 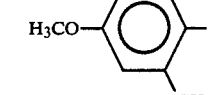 |
| 1-7 | 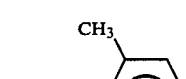 |
| 1-8 | 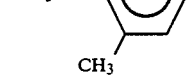 |

TABLE VI-1-continued
($R^1$ substituents of compounds represented by
the formula $R^1-\overset{\overset{O}{\|}}{C}-\overset{\overset{CH_3}{|}}{CH_2}$ which are
used as one of the starting materials for
the compounds represented by the general
formula (I) listed in Table I.)
| Compound No. | $R^1$ |
|---|---|
| 1-9 | 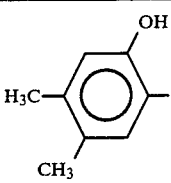 |
| 1-10 | 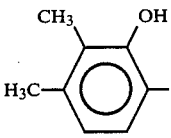 |
| 1-11 | 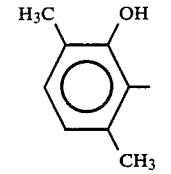 |
| 1-12 | 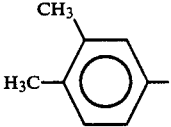 |
| 1-13 | 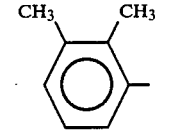 |
| 1-14 | 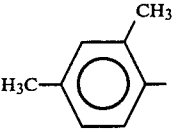 |
| 1-15 | 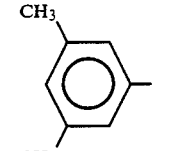 |
| 1-16 | 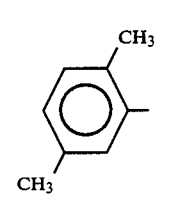 |
| 1-17 | 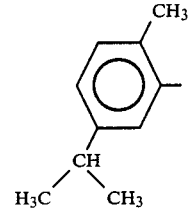 |
| 1-18 | 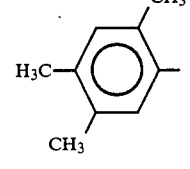 |
| 1-19 | 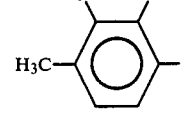 |
| 1-20 | 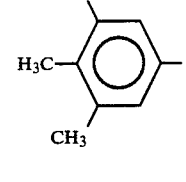 |
| 1-21 | 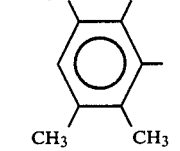 |
| 3-1 | 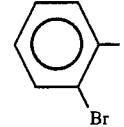 |
| 3-2 | 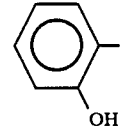 |
| 3-3 | 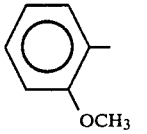 |

TABLE VI-1-continued ($R^1$ substituents of compounds represented by the formula $R^1-\overset{\overset{O}{\|}}{C}-\overset{\overset{CH_3}{|}}{C}H_2$ which are used as one of the starting materials for the compounds represented by the general formula (I) listed in Table I.)

| Compound No. | $R^1$ |
|---|---|
| 3-4 | 2-(CF$_3$)phenyl |
| 3-5 | 2-methylphenyl |
| 3-6 | 2-ethylphenyl |
| 3-7 | 2-isopropylphenyl |
| 3-8 | 2-vinylphenyl |
| 3-9 | 2-(pyrrolidin-1-yl)phenyl |
| 3-10 | 2-phenylphenyl (biphenyl-2-yl) |
| 3-11 | 3-bromophenyl |
| 3-12 | 3-(CF$_3$)phenyl |
| 3-13 | 3-methylphenyl |
| 3-14 | 3-vinylphenyl |
| 3-15 | 3-(cyclohex-1-en-1-yl)phenyl |
| 3-16 | 3-phenylphenyl (biphenyl-3-yl) |
| 3-17 | 3-methyl-4-hydroxyphenyl |
| 3-18 | 3-methoxy-5-fluorophenyl |
| 3-19 | 3-chloro-4-methoxyphenyl |

TABLE VI-1-continued ($R^1$ substituents of compounds represented by
the formula $R^1-\overset{O}{\underset{\|}{C}}-\overset{CH_3}{\underset{|}{C}}H_2$ which are used as one of the starting materials for the compounds represented by the general formula (I) listed in Table I.)

| Compound No. | $R^1$ |
|---|---|
| 3-20 | 4-Cl, 3-OCH₃-phenyl |
| 3-21 | 2-OCH₃, 4-Cl-phenyl |
| 3-22 | 2-OCH₃, 3-CH₃-phenyl |
| 3-23 | 3-CH₃, 4-OCH₃-phenyl |
| 3-24 | 2-OCH₃, 4-OCH₃-phenyl |
| 3-25 | 3-OCH₃, 2-F-phenyl (H₃CO, F substituted phenyl) |
| 3-26 | 3-OCH₃, 4-CH₃-phenyl |
| 3-27 | 3-OCH₃, 2,4-(CH₃)₂-phenyl |
| 3-28 | 3-OCH₃, 2,4-(CH₃)₂-phenyl (with CH₃ groups) |
| 3-29 | 2-OCH₃, 4-CH₃, 5-Cl-phenyl |
| 3-30 | 2-OCH₃, 3-CH₃, 5-Cl-phenyl |
| 3-31 | 2-OCH₃, 3-CH₃, 4-Cl-phenyl |
| 3-32 | 2-Cl, 3-OCH₃, 5-CH₃-phenyl |
| 3-33 | 2,6-Cl(CH₃)-phenyl |
| 3-34 | 2-CH₃, 4-F-phenyl |
| 3-35 | 4-CH₃, 2-F-phenyl |

TABLE VI-1-continued (R¹ substituents of compounds represented by the formula $R^1-\overset{\overset{O}{\|}}{C}-\overset{\overset{CH_3}{|}}{CH_2}$ which are used as one of the starting materials for the compounds represented by the general formula (I) listed in Table I.)

| Compound No. | R¹ |
|---|---|
| 3-36 | 4-chloro-2,3-dimethylphenyl (Cl, CH₃, CH₃) |
| 3-37 | 4-chloro-2,6-dimethylphenyl (Cl, CH₃, CH₃) |
| 3-38 | 4-fluoro-2,3-dimethylphenyl (F, CH₃, CH₅) |
| 3-39 | 3-fluorophenyl (F) |
| 3-40 | 3-fluorophenyl (F) |
| 4-1 | 4-(trifluoromethyl)phenyl (F₃C—) |
| 4-2 | 2-methoxy-4-fluorophenyl (OCH₃, F) |
| 4-3 | 2-methyl-6-hydroxyphenyl (CH₃, OH) |
| 4-4 | 2,3,4-trimethoxyphenyl (CH₃O, OCH₃, CH₃O) |
| 4-5 | 3-methyl-4-methoxy-5-chloro-6-methylphenyl (OCH₃, CH₃, Cl, CH₃) |
| 4-6 | 5-methoxy-1,2,3,4-tetrahydronaphthyl (CH₃O, H) |
| 4-7 | 5-hydroxy-1,2,3,4-tetrahydronaphthyl (HO, H) |
| 4-8 | 5-(dimethylamino)-1,2,3,4-tetrahydronaphthyl ((CH₃)₂N, H) |
| 4-9 | 5-methoxynaphthyl (CH₃O) |

TABLE VI-2

($R^1$ and $R^2$ substituents of Compounds represented by the formula $R^1-\overset{O}{\underset{\|}{C}}-\overset{R^2}{\underset{|}{CH}}_2$ and $-N\overset{R_a}{\underset{R_b}{\diagup}}$ groups of compounds represented by the formula $HN\overset{R_a}{\underset{R_b}{\diagup}}$ which are used as starting materials for the compounds represented by the general formula (I) listed in Table II.)

| Compound No. | $R^1$ | $R^2$ | $-N\overset{R_a}{\underset{R_b}{\diagup}}$ |
|---|---|---|---|
| 4-10 | 2,3-(CH₃)₂-phenyl | CH₃ | piperidino |
| 4-11 | 2,3,4-(CH₃O)₃-phenyl | CH₃ | piperidino |
| 4-12 | 3-CH₃O-4,6-(CH₃)₂-phenyl | CH₃ | piperidino |
| 4-13 | 2-CH₃-3-OCH₃-5-CH₃-phenyl | CH₃ | piperidino |
| 4-14 | 2,3-(CH₃)₂-phenyl | C₂H₅ | pyrrolidino |
| 4-15 | 3,4-(CH₃)₂-phenyl | C₂H₅ | pyrrolidino |
| 4-16 | 3-CH₃O-4,6-(CH₃)₂-phenyl | C₂H₅ | pyrrolidino |
| 4-17 | 2-CH₃-3-OCH₃-5-CH₃-phenyl | C₂H₅ | pyrrolidino |
| 4-18 | 3,4-(CH₃)₂-phenyl | H | pyrrolidino |
| 4-19 | 2-CH₃-3-OCH₃-5-CH₃-phenyl | H | pyrrolidino |
| 4-20 | 3-CH₃O-4,6-(CH₃)₂-phenyl | H | pyrrolidino |
| 2-1 | 6-CH₃O-5,6,7,8-tetrahydronaphthyl | CH₃ | pyrrolidino |
| 2-2 | 6-C₂H₅O-5,6,7,8-tetrahydronaphthyl | CH₃ | pyrrolidino |

TABLE VI-2-continued (R¹ and R² substituents of Compounds represented by the formula $R^1-\overset{O}{\underset{\|}{C}}-\overset{R^2}{\underset{|}{CH_2}}$ and $-N\overset{R_a}{\underset{R_b}{\diagdown}}\Big)$ groups of compounds represented by the formula $HN\overset{R_a}{\underset{R_b}{\diagdown}}\Big)$ which are used as starting materials for the compounds represented by the general formula (I) listed in Table II.)

| Compound No. | R¹ | R² | $-N\overset{R_a}{\underset{R_b}{\diagdown}}$ |
|---|---|---|---|
| 2-3 | 6-(C₃H₇O)-5,6,7,8-tetrahydronaphth-2-yl | CH₃ | pyrrolidin-1-yl |
| 2-4 | 6-(CH₃O)-5,6,7,8-tetrahydronaphth-2-yl | CH₃ | piperidin-1-yl |
| 2-5 | 6-(C₃H₇O)-5,6,7,8-tetrahydronaphth-2-yl | CH₃ | piperidin-1-yl |
| 2-6 | 6-Cl-5,6,7,8-tetrahydronaphth-2-yl | CH₃ | pyrrolidin-1-yl |
| 2-7 | 6-Cl-5,6,7,8-tetrahydronaphth-2-yl | CH₃ | piperidin-1-yl |
| 2-8 | 6-CH₃-5,6,7,8-tetrahydronaphth-2-yl | CH₃ | pyrrolidin-1-yl |
| 2-9 | 5,6,7,8-tetrahydronaphth-2-yl | CH₃ | pyrrolidin-1-yl |
| 2-10 | 6-(CH₃O)-5,6,7,8-tetrahydronaphth-2-yl | CH₃ | $-N(C_2H_5)_2$ |
| 2-11 | 6-(CH₃O)-5,6,7,8-tetrahydronaphth-2-yl | C₂H₅ | pyrrolidin-1-yl |
| 2-16 | 6-(CH₃O)-5,6,7,8-tetrahydronaphth-2-yl | H | pyrrolidin-1-yl |
| 2-17 | 6-(CH₃O)-5,6,7,8-tetrahydronaphth-2-yl | H | pyrrolidin-1-yl |
| 2-18 | 6-(CH₃O)-5,6,7,8-tetrahydronaphth-2-yl | H | pyrrolidin-1-yl |

TABLE VI-2-continued ($R^1$ and $R^2$ substituents of Compounds represented by the formula $R^1-\overset{O}{\underset{\|}{C}}-\overset{R^2}{\underset{|}{C}}H_2$ and $-N\begin{matrix}R_a \\ R_b\end{matrix}$ groups of compounds represented by the formula $HN\begin{matrix}R_a \\ R_b\end{matrix}$ which are used as starting materials for the compounds represented by the general formula (I) listed in Table II.)

| Compound No. | $R^1$ | $R^2$ | $-N\begin{matrix}R_a \\ R_b\end{matrix}$ |
|---|---|---|---|
| 2-12 | 5,6,7,8-tetrahydro-2-methoxy-3-naphthyl (H on position 1) | CH₃ | pyrrolidino |
| 2-13 | 5,6,7,8-tetrahydro-2-methoxy-3-naphthyl (H on position 1) | CH₃ | piperidino |
| 2-14 | 5,6,7,8-tetrahydro-2-chloro-3-naphthyl (H on position 1) | CH₃ | pyrrolidino |
| 2-15 | 5,6,7,8-tetrahydro-2-methyl-3-naphthyl (H on position 1) | CH₃ | pyrrolidino |

TABLE VII

| Compound No. | Yield % | Melting Point of HCl Salt (°C.) | Solvent for Recrystallization |
|---|---|---|---|
| 1-1 | 42 | 183–186 | (Acetone Et₂O) |
| 1-2 | 77.0 | 179–180 | (Acetone) |
| 1-3 | 68.2 | 159–161 | (CH₂Cl₂ Acetone) |
| 1-4 | 48.9 | 154–156 | (AcOEt Acetone Et₂O) |
| 1-5 | 65.8 | 194–195 | (MeOH Acetone) |
| 1-6 | 90.0 | 160–161 | (CH₂Cl₂ AcOEt) |
| 1-7 | 61.8 | 158–159 | (CH₂Cl₂ AcOEt) |
| 1-8 | 68.2 | 128–131 | (Acetone Et₂O) |
| 1-9 | 72.1 | 195.5–196.5 | (CH₂Cl₂ AcOEt) |
| 1-10 | 35.0 | 183–185 | (CH₂Cl₂ AcOEt) |
| 1-11 | 20.3 | 186–188 | (CH₂Cl₂ Acetone) |
| 1-12 | 79.4 | 180–181 | (CH₂Cl₂ Acetone) |
| 1-13 | 28 | 149–151 | (Acetone MeOH) |
| 1-14 | 57.8 | 173–174 | (CH₂Cl₂ AcOEt) |
| 1-15 | 68.4 | 210–211 | (CH₂Cl₂ AcOEt) |
| 1-16 | 59.8 | 164–166 | (CH₂Cl₂ Acetone) |
| 1-17 | 61.5 | 140–142 | (CH₂Cl₂ AcOEt) |
| 1-18 | 57.2 | 179–180 | (CH₂Cl₂ Acetone) |
| 1-19 | 92.4 | 211–213 | (CH₂Cl₂) |
| 1-20 | 50.8 | 197–198 | (MeOH Acetone) |
| 1-21 | 41.9 | 167–168 | (CH₂Cl₂ Acetone) |
| 3-1 | 52.7 | 134–136 | (MeOH Acetone) |
| 3-2 | 90.6 | 104–106 | (Acetone) |
| 3-3 | 89.2 | 138–140 | (CH₂Cl₂ Acetone) |
| 3-4 | 19.2 | 148–149 | (MeOH Acetone) |
| 3-5 | 73.4 | 144–145.5 | (MeOH Acetone) |
| 3-6 | 75.0 | 138–139 | (MeOH Acetone) |
| 3-7 | 57.8 | 116–118 | (Acetone) |
| 3-8 | 73.2 | 143–144 | (MeOH Acetone) |
| 3-9 | 39.2 | 101–105 | (Acetone) |
| 3-10 | 43.0 | 138–139 | (MeOH AcOEt) |
| 3-11 | 80.0 | 152.5–154 | (MeOH Acetone) |
| 3-12 | 32.9 | 144–145 | (Acetone Et₂O) |
| 3-13 | 97.7 | 166–168 | (MeOH Acetone) |
| 3-14 | 79.1 | 151–153 | (MeOH Acetone) |
| 3-15 | 50.8 | 142–144 | (Acetone) |
| 3-16 | 55.0 | 157–159 | (MeOH Acetone) |
| 3-17 | 83.0 | 156–158 | (MeOH Acetone) |
| 3-18 | 38.0 | 144–146 | (CH₂Cl₂ Acetone) |
| 3-19 | 36.1 | 125–127 | (Acetone) |
| 3-20 | 64.0 | 140–141.5 | (AcOEt Acetone) |
| 3-21 | 82.2 | 166–167 | (Acetone) |
| 3-22 | 86.7 | 143–144 | (CH₂Cl₂ AcOEt) |
| 3-23 | 44.6 | 152–153.5 | (MeOH Acetone) |
| 3-24 | 87.0 | 126–128 | (MeOH Acetone) |
| 3-25 | 48.0 | 158–159 | (MeOH Acetone) |
| 3-26 | 52.4 | 142–143 | (Acetone AcOEt) |
| 3-27 | 31.0 | 154–155 | (CH₂Cl₂ Acetone) |
| 3-28 | 34.7 | 147–148 | (CH₂Cl₂ AcOEt) |
| 3-29 | 84.9 | 184–185 | (Acetone) |
| 3-30 | 64.1 | 149–150 | (Acetone) |
| 3-31 | 63.3 | 206–207 | (CH₂Cl₂ Acetone) |
| 3-32 | 81.1 | 186–188 | (CH₂Cl₂ AcOEt) |
| 3-33 | 23.7 | 172–173 | (CH₂Cl₂ AcOEt) |

TABLE VII-continued

| Compound No. | Yield % | Melting Point of HCl Salt (°C.) | Solvent for Recrystallization |
|---|---|---|---|
| 3-34 | 42.4 | 174–175 | (CH$_2$Cl$_2$) |
| 3-35 | 20.0 | 186–187 | (CH$_2$Cl$_2$ AcOEt) |
| 3-36 | 58.9 | 204–206 | (MeOH AcOEt) |
| 3-37 | 21.2 | 139–140 | (CH$_2$Cl$_2$ AcOEt) |
| 3-38 | 72.1 | 188–189 | (CH$_2$Cl$_2$ Acetone) |
| 3-39 | 32.7 | 121–122 | (Acetone) |
| 3-40 | 64.7 | 152–153.5 | (Acetone) |
| 4-1 | 44.8 | 154–156 | (Acetone AcOEt) |
| 4-2 | 38.0 | 144–146 | (CH$_2$Cl$_2$ Acetone) |
| 4-3 | 47.2 | 155–156 | (CH$_2$Cl$_2$ Acetone) |
| 4-4 | 63.2 | 92–93 | (Acetone AcOEt) |
| 4-5 | 50.0 | 165–166 | (CH$_2$Cl$_2$ AcOEt) |
| 4-8 | 17.3 | 176–178 | (Et$_2$O Hexane) |
| 4-9 | 62.4 | 153–157 | (CH$_2$Cl$_2$ AcOEt) |
| 4-10 | 51.0 | >225 | (HeOH) |
| 4-11 | 50.0 | — | — |
| 4-12 | 56.0 | 185–186 (dec) | (CH$_2$Cl$_2$ Acetone) |
| 4-13 | 51.2 | 154–156 | (CH$_2$Cl$_2$ Acetone) |
| 4-14 | 55.6 | 156–157 | (CH$_2$Cl$_2$ AcOEt) |
| 4-15 | 59.3 | 163–164 | (MeOH Acetone) |
| 4-16 | 47.3 | 190–191 | (CH$_2$Cl$_2$ AcOEt) |
| 4-17 | 81.5 | 141–143 | (MeOH AcOEt) |
| 2-1 | 83.9 | 150–151 | (CH$_2$Cl$_2$ AcOEt) |
| 2-3 | 86.6 | 161–162 | (CH$_2$Cl$_2$ AcOEt) |
| 2-4 | 73.1 | 158–159 | (MeOH Acetone) |
| 2-6 | 85.9 | 184–185 | (CH$_2$Cl$_2$ AcOEt) |
| 2-9 | 56.2 | 122–123 | (CH$_2$Cl$_2$ AcOEt) |
| 2-10 | 64.0 | 120–121 | (AcOEt) |
| 2-11 | 62.8 | 164–165 | (CH$_2$Cl$_2$ AcOEt) |
| 2-12 | 90.4 | 162–163 | (CH$_2$Cl$_2$ AcOEt) |
| 2-16 | 83.2 | 171–172 | (MeOH Acetone) |

EXAMPLE 2

1-(4-Trifluoromethylphenyl)-2-methyl-3-pyrrolidino-1-propanone (Compd. No. 4-1) hydrochloride.

A mixture of 1-(4-trifluoromethylphenyl)-1-propanone (2.50g), paraformaldehyde (1.10g), pyrrolidine hydrochloride (1.60g), and hydrochloric acid (0.1 ml) was refluxed for 16 hours. The mixture was evaporated in vacuo to give the residue. The residue was partitioned into water and ethyl acetate. The aqueous layer was neutralized with ammonia water and then extracted with ethyl acetate. The organic layer was dried over anhydrous magnesium sulfate and then filtered. The filtrate was evaporated in vaccuo to give 1-(4-trifluoromethylphenyl)-2-methyl-3-pyrrolidino-1propanone (1.58g; yield: 44.8%) as an oil.

IR $\nu_{max}^{neat}$: 1690 cm$^{-1}$

NMR δ (CDCl$_3$, TMS): 1.25 (d,3H, J=7.0 Hz;

—COCH(CH$_3$)CH$_2$—), 1.4—2.1(m,4H —N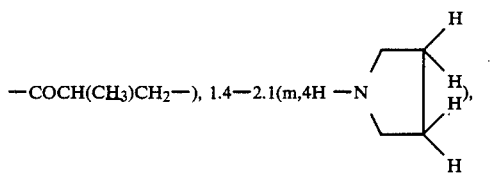), 2.3—3.2 (m, 6H, —CH$_2$N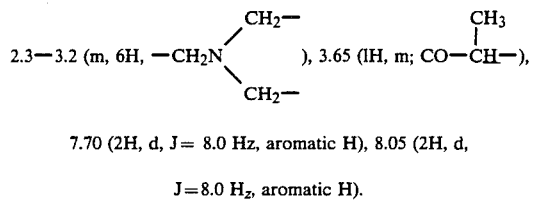), 3.65 (1H, m; CO—CH(CH$_3$)—), 7.70 (2H, d, J= 8.0 Hz, aromatic H), 8.05 (2H, d, J=8.0 H$_z$, aromatic H).

Mass m/z (relative intensity): 285 (2.21, M$^+$), 214 (100); 173 (100), 145 (100), 95 (29.7), 84 (100).

The free base was dissolved in ethyl ether, reacted by introducing dry hydrochloride gas, and then filtered off. The crude crystals were recrystallized from acetone- AcOEt to give the HCl salts as colorless prisms (1.43 g), m.p. 154°–156° C.

EXAMPLE 3

1-(4-Methoxy-5,6,7,8-tetrahydro-1-naphthyl)-2-methyl-3-pyrrolidino-1-propanone (compd. No. 2-1) hydrochloride.

A mixture of 1-(4-methoxy-5,6,7,8-tetrahydro-1-naphthyl)-1-propanone (4.37g), paraformaldehyde (1.80g), pyrrolidine hydrochloride (3.23g), and hydrochloric acid (0.2 ml) in isopropyl alcohol (50 ml) was refluxed for 8 hours. The reaction mixture was evaporated in vacuo to give the residue. The residue was partitioned into water and ethyl ether. The aqueous layer was extracted, neutralized with ammonia water, and then extracted with ethyl ether. The organic layer was dried over anhydrous magnesium sulfate and then filtered. The filtrate was evaporated in vacuo to give 1-(4-methoxy-5,6,7,8-tetrahydro-1-naphthyl)-2-methyl-3-pyrrolidino -1-propanone. (5.06; yield: 83.9%).

IR $\nu_{max}^{neat}$: 1690 cm$^{-1}$

NMR δ (CDCl$_3$, TMS): 1.20 (d, 3H, J=7.0 Hz;

—COCH(CH$_3$)CH$_2$—), 1.4—2.1 (m, 8H, 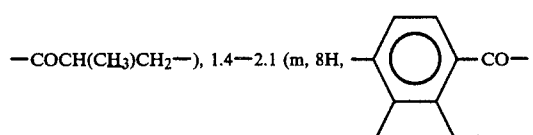

and —N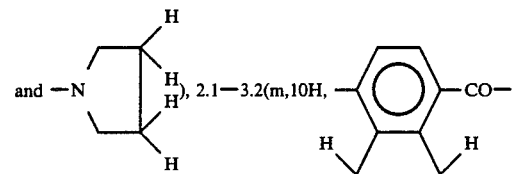), 2.1—3.2(m,10H, and —CH₂N(CH₂—)(CH₂—) ), 3.86 (s, 3H, CH₃O—[ring]—CO—), 6.70 (d, 1H, J=8.0 Hz; —[naphthyl-H]—CO—), 7.53 (d, 1H, J=8.0 Hz; —[naphthyl-H]—CO—)

Mass m/z (relative intensity): 301 (M+, 4.87), 230 (35.3), 215 (24.3), 189 (19.3), 187 (10.3), 84 (100).

The free base was dissolved in ethyl ether, reacted by introducing dry hydrochloride gas, and then filtered off. The crude crystals were recrystallized from CH₂Cl₂ - AcOEt to give the HCl salts (3.60 g) as colorless prisms, m.p. 150°–151° C.

EXAMPLE 4

2-Methyl-1-(2,3-dimethylphenyl)-3-pyrrolidino-1-propanone (Compd. No. 1-13) hydrochloride.

A mixture of 1-(2,3-dimethylphenyl)-1-propanone (11.2 g), paraformaldehyde (2.70 g), pyrrolidine-hydrochloride (9.7g), and hydrochloric acid (0.5 ml) in isopropyl alcohol (15 ml) was refluxed for 8.5 hours. The reaction mixture was evaporated in vacuo to give the residue. The residue was dissolved in water and then washed with ethyl acetate. The aqueous layer was extracted with dichloromethane and then dried over anhydrous magnesium sulfate. The mixture was filtered and then the filtrate was evaporated in vacuo to give the residue. The residue was recrystallized from CH₂Cl₂ - AcOEt to give 2-methyl-1-(2,3-dimethylphenyl)-3-pyrrolidino-1-propanone hydrochloride (13.1 g, Y: 64.7%) as colorless prisms, m.p. 149°–151° C. IR ν (the free base)$_{max}^{neat}$: 1690 cm$^{-1}$ NMR (the free base) δ (CDCl₃, TMS): 1.20 (d, 3H, J = 7.0 Hz, —COCH(CH₃)CH₂—), 1.5–2.0 (m, 4H, —N[pyrrolidine]), 2.1–3.1 (m, 6H, —CH₂N(CH₂—)(CH₂—) ), 2.66 (s, 6H, CH₃,CH₃—[ring]—CO—), 3.1–3.8 (m, 1H, —COCH(CH₃)CH₂—), 6.9–7.5 (m, 3H, H—[ring]—)

Mass (the free base) m/z (relative intensity): 245 (M+, 0.0097), 174 (30.5), 159 (40.2), 133 (76.3), 105 84 (100).

EXAMPLE 5

1-(4-Methoxy-5,6,7,8-tetrahydro-1-naphthyl)-4-pyrrolidino-1-butanone (Compd. No. 2-17) hydrochloride.

A mixture of 1-(4-methoxy-5,6,7,8-tetrahydro-1-naphthyl)-4-chloro-1-butanone (4.0g), pyrrolidine (4.27g), potassium iodide (0.3g) and potassium carbonate (2.0g) in absolute N,N-dimethylformamide (30 ml) was stirred at 60° C. for 10 hours. The reaction mixture was filtered and then the filtrate was partitioned into water and ethyl acetate. The organic layer was extracted, washed with water and then dried over anhydrous magnesium sulfate. The mixture was filtered and the filtrate was evaporated in vacuo to give the residue. The residue was dissolved in ethyl ether. The ethyl ether solution was extracted with 1N hydrochloric acid. The aqueous layer was neutralized with ammonia water and then extracted with ethyl ether. The ethyl ether was dried over anhydrous magnesium sulfate. The solution was filtered and the filtrate was evaporated in vacuo to give 1-(4-methoxy-5,6,7,8-tetrahydro-1-naphthyl)-4-pyrrolidino-1-butanone (3.7 g; yield: 82%) as an oil.

IR ν$_{max}$

NMR δ (CDCl₃, TMS): 1.2–2.3 (m, 10H, —[tetrahydronaphthyl]—COCH₂CH₂CH₂— and —CH₂N(pyrrolidine) ), 2.3–2.9 (m, 10H, —[tetrahydronaphthyl]—CO— and —CH₂N(pyrrolidine) ), 2.8–3.2 (m, 2H, —COCH₂CH₂—), 3.99 (brs, 3H, CH₃O—[ring]—CO), 6.83 (d, 1H, J=7.0 Hz;

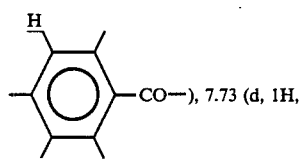, 7.73 (d, 1H,

J=7.0 Hz; 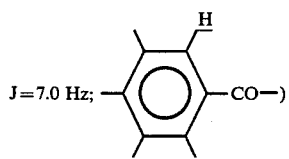)

Mass m/z (relative intensity): 301 (M+, 9.2) 189 (7.7), 98 (22.0), 97 (136.1), 96 (6.1), 85 (5.9), 84

The free base was dissolved in ethyl ether, reacted by introducing dry hydrochloride gas, and then filtered off. The crude crystals were recrystallized from CH$_2$Cl$_2$ - AcOEt to give the HCl salts as colorless prisms, m.p. 177°–178° C.

By using the compounds of the formulae

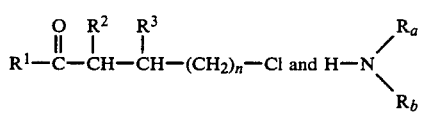

as starting materials (the combinations of R$^1$, R$^2$, R$^3$, n and

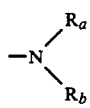

being the same as in Tables I and II) and by following the procedures of the above examples, there can be obtained all of the compounds of this invention represented by the general formula (I). Examples of the combinations of R$^1$, R$^2$, R$^3$, n and

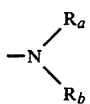

in said two starting compounds are shown in Table VIII. (Compound Nos. in the table correspond to those in Table VI).

TABLE VIII

| Compound No. | R$^1$ | R$^2$ | R$^3$ | n | $-N\begin{subarray}{l}R_a\\R_b\end{subarray}$ |
|---|---|---|---|---|---|
| 1-13 | 2,3-(CH$_3$)$_2$-C$_6$H$_3$- | H | CH$_3$ | 0 | pyrrolidino |
| 4-1 | 4-F$_3$C-C$_6$H$_4$- | H | CH$_3$ | 0 | pyrrolidino |
| 2-1 | 5-CH$_3$O-5,6,7,8-tetrahydronaphthyl | CH$_3$ | H | 0 | pyrrolidino |
| 2-10 | 5-CH$_3$O-5,6,7,8-tetrahydronaphthyl | CH$_3$ | H | 0 | N(C$_2$H$_5$)$_2$ |
| 2-11 | 5-CH$_3$O-5,6,7,8-tetrahydronaphthyl | C$_2$H$_5$ | H | 0 | pyrrolidino |
| 2-16 | 5-CH$_3$O-5,6,7,8-tetrahydronaphthyl | H | H | 0 | pyrrolidino |
| 2-17 | 5-CH$_3$O-5,6,7,8-tetrahydronaphthyl | H | H | 1 | pyrrolidino |
| 2-18 | 5-CH$_3$O-5,6,7,8-tetrahydronaphthyl | H | CH$_3$ | 0 | pyrrolidino |

EXAMPLE 6

1-(4-Methoxy-5,6,7,8-tetrahydro-1-naphthyl)-3-methyl-3-pyrrolidino-1-propanone (Compd. No. 2-18) hydrochloride.

A solution of 1-(4-methoxy-5,6,7,8-tetrahydro-1-naphthyl)-2-butene-1-one (3.0 g) and pyrrolidine (1.85 g) in ethanol (100 ml) was stirred for 3 hours at room temperature. The mixture was evaporated in vacuo to give the residue. The residue was partitioned into water and ethyl ether The ethyl ether was washed with water. The organic layer was extracted with 2N hydrochloric acid. The aqueous layer was neutralized with ammonia water and then extracted with ethyl ether. The ethyl ether was dried over anhydrous magnesium sulfate and then filtered. The filtrate was evaporated in vacuo to give 1-(4-methoxy-5,6,7,8-tetrahydro-1-naphthyl)-3-methyl-3-pyrrolidino-1-propanone (2.31 g, Yield: 53.6%) as an oil.

IR $\nu_{max}^{neat}$: 1680 cm$^{-1}$

NMR δ (CDCl$_3$, TMS): 1.11 (d, 3H, J=7.0 Hz; —CH$_3$),

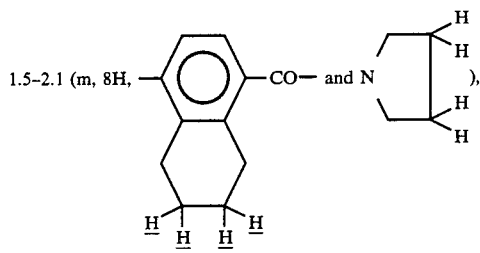

1.5-2.1 (m, 8H,

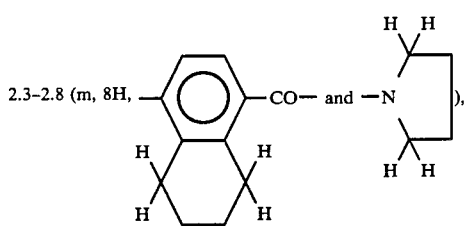

2.3-2.8 (m, 8H, 2.8-3.2 (m, 3H, —COCH$_2$CH—), 3.86 (s, 3H, —OCH$_3$),

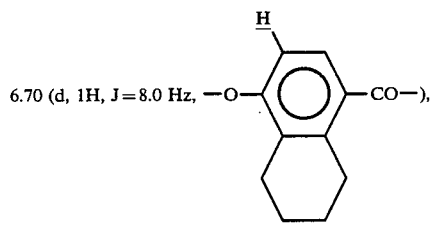

6.70 (d, 1H, J=8.0 Hz, —O—

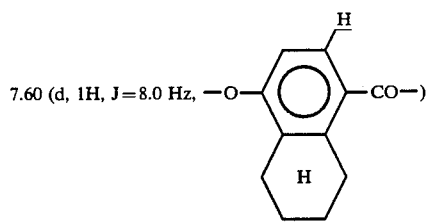

7.60 (d, 1H, J=8.0 Hz, —O—

Mass m/z (relative intensity): 301 (M+, 5.6), 230 (21.5), 215 (33.0), 189 (21.4), 187 (14.7), 98 (100), 97 (30.7).

The free base was dissolved in ethyl ether, reacted by introducing dry hydrochloride gas, and then filtered off. The crude crystals were recrystallized from CH$_2$Cl$_2$-AcOEt to give the HCl salts as colorless prisms, m.p. 149°-150° C.

By using the compounds of the formulae

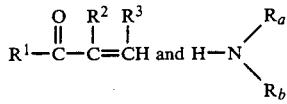

as starting materials (the combinations of R$^1$, R$^2$, R$^3$ and

being the same as in Tables I and II) and by following the procedures of the above example, there can be obtained the compounds of this invention represented by the general formula (I) in which n is 0. Hydrochlorides of these compounds can be obtained by making the reaction solution acidic with dilute hydrochloric acid and then treating it similarly to Example 4. Examples of the compounds obtained by this method are shown in Table IX.

TABLE IX

| Compound No. | Yield % | Melting Point of HCl Salt (°C.) | Solvent for Recrystallization |
|---|---|---|---|
| 4-18 | 92.2 | 123-125 | (Acetone) |
| 4-19 | 100 | 124-126 | (Acetone) |
| 4-20 | 100 | 157-158 | (CH$_2$Cl$_2$ AcOEt) |

Examples of the combinations of R$^1$, R$^2$, R$^3$ and

in said two starting compounds are shown in Table X. (Compound Nos. in the table correspond to those in Table IX).

TABLE X

| Compound No. | R$^1$ | R$^2$ | R$^3$ | —N(R$_a$)(R$_b$) |
|---|---|---|---|---|
| 4-18 | 3,4-dimethylphenyl | H | CH$_3$ | pyrrolidino |
| 4-19 | 2-methoxy-5-methylphenyl | OCH$_3$ | H | CH$_3$ pyrrolidino |

TABLE X-continued

| Compound No. | R¹ | R² | R³ | −N⟨Ra/Rb⟩ |
|---|---|---|---|---|
| 4-20 | CH₃, CH₃O−⟨phenyl⟩−CH₃ | H | CH₃ | N⟨pyrrolidino⟩ |

EXAMPLE 7 d-2-Methyl-1-(4-trifluoromethylphenyl)-3-pyrrolidino-1-propanone hydrochloride(4-1-d hydrochloride)

(i) In 150 ml of isopropanol were dissolved 24.7 g of dl-2-methyl-1-(4-trifluoromethylphenyl)-3-pyrrolidino-1-propanone and D-acetylphenylglycine ($[α]_D^{20} = -212.8°$, c=1.0, ethanol). After the salt was formed, the solution was concentrated under reduced pressure to 60 ml and then allowed to stand overnight in a refrigerator. The deposited crystalline material was isolated by filtration, and the crude crystalline material was recrystallized from 30 ml of isopropanol to give 13.4 g of D-acetylphenylglycine salt of d-2-methyl-1-(4-trifluoromethylphenyl)-3-pyrrolidino-1-propanone having $[α]_D^{20}$ of $-39.2°$ (c=1.0, methanol).

(ii) In 150 ml of water was dissolved 10.3 g of D-acetylphenylglycine salt of d-2-methyl-1-(4-trifluoromethylphenyl)-3-pyrrolidino-1-propanone obtained in (i). To the resulting solution 150 ml of ethyl ether was added. The solution was neutralized with a 4% aqueous sodium bicabonate solution and extracted with ether. The ether layer was extracted with 1N HCl. The aqueous layer was extracted several times with dichloromethane, and then the dichloromethane layer was dried over anhydrous magnesium sulfate. Subsequently, the solvent was distilled off under reduced pressure, and the residue was recrystallized from dichloromethane-ethyl acetate to give 5.1 g of d-2-methyl-1-(4-trifluoromethylphenyl)-3-pyrrolidino-1-propanone hydrochloride having $[α]_D^{20}$ of $+44.05°$ (c=1.0, methanol) and a melting point of 155° to 157° C.

EXAMPLE 8 l-2-Methyl-1-(4-trifluoromethylphenyl)-3-pyrrolidino-1-propanone hydrochloride(4-1-l hydrochloride)

(i) L-Acetylphenylglycine salt of l-2-methyl-1-(4-trifluoromethylphenyl)-3-pyrrolidino-1-propanone having $[α]_D^{20}$ of $+39.3°$ (c=1.0, methanol) was prepared in the same manner as in Example 7, using L-acetylphanylglycine ($[α]_D^{20} = 21.9°$, c=1.0, ethanol) instead of using the D-acetylphenylglycine.

(ii) L-Acetylphenylglycine salt of l-2-methyl-1-(4-trifluoromethylphenyl)-3-pyrrolidino-1-propanone prepared in above-mentioned (i) was treated in the same manner as in Example 7 (ii) to give l-2-methyl-1-(4-trifluoromethylphenyl)-3-pyrrolidino-1-propanone hydrochloride having $[α]_D^{20}$ of $-43.3°$ (c=1.0, methanol) and a melting point of 155° to 157° C.

EXAMPLE 9 l-2-Methyl-1-(4-trifluoromethylphenyl)-3-pyrrolidino-1-propanone hydrochloride (i) In 1400 ml of ethyl acetate were dissolved 306 g of dl-2-methyl-1-(4-trifluoromethylphenyl)-3-pyrrolidino-1-propanone and 210 g of L-acetylphenylglycine ($[α]_D^{20} = +210.0°$, c=1.0, methanol). After the salt was formed, the solution was allowed to stand overnight at room temperature and then was stirred at about 5° C. for 3 hours. The deposited crystals were filtrated and dried under reduced pressure to give 219 g of first crystals of crude L-acetylphenylglycine salt of l-2-methyl-1-(4-trifluoromethylphenyl)-3-pyrrolidino-1-propanone (yield: 43%, content: about 93%, optical purity: about 98%).

The filtrate was concentrated to 574 g under reduced pressure, allowed to stand at room temperature for 2 days and then stirred at about 5° C. for 3 hours. The deposited crystals were filtrated and then dried under reduced pressure to obtain 175 g of second crystals of crude L-acetylphenylglycine salt of l-2-methyl-1-(4-trifluoromethylphenyl)-3-pyrrolidino-1-propanone (content: about 85%, optical purity: about 92%).

(ii) To the first and second crystal (total amount: 394 g) prepared in above (i) was added 630 ml of a 10% aqueous sodium chloride solution, 950 ml of ethyl acetate, and 60 ml of aqueous ammonia. The ethyl acetate layer was extracted, washed with 315 ml of a 10% aqueous sodium chloride solution and then dried over anhydrous magnesium sulfate. Subsequently, 29 g of gaseous hydrogen chloride was gradually introduced into the ethyl acetate solution under cooling (25° C. or below). The resulting solution was stirred at an inner temperature of about 5° C. The crystals were filtrated, washed with 370 ml of ethyl acetate, and then dried under reduced pressure to give 217 g of (-2-methyl-1-(4-trifluoromethylphenyl)-3-pyrrolidino-1-propanone hydrochloride (content: 99%, optical purity: 97%).

(iii) The l-2-methyl-1-(4-trifluoromethylphenyl)-3-pyrrolidino-1-propanone hydrochloride prepared in above (ii) was treated in the same manner as in (ii) to give highly purified l-2-methyl-1-(4-trifluoromethylphenyl)-3-pyrrolidino-1-propanone hydrochloride with a content of 99.5% or more, an optical purity of 99.5% or more and $[α]_D^{20}$ of $-45.0°$ (c=1.0, methanol) and a melting point of 156° to 159° C.

EXAMPLE 10 d-2-Methyl-1-(4-trifluoromethylphenyl)-3-pyrrolidinol-propanone hydrochloride (i) In 35 ml of isopropanol were dissolved 14.3 g (50.0 mmol) of dl-2-methyl-1-(4-trifluoromethylphenyl)-3-pyrrolidino-1-propanone and 9.66 g (50.0 mmol) of D-acetylphenylglycine ($[α]_D^{20} = -210.0°$, c=1.0, methanol). After the salt was formed, the solution was allowed to stand overnight in a refrigerator. Crystals were filtrated, washed with ether, and then dried under reduced pressure to give 12.5 g of crude D-acetylphenylglycine salt of d-2-methyl-1-(4-trifluoromethylphenyl)-3-pyrrolidino-1-propanone [content: about 90% or more, optical purity: about 97% or more, $[α]_D^{20}$ of $-39°$ to $-40°$, (c=1.0, methanol)].

(ii) The crude D-acetylphenylglycine salt of d-2-methyl-1-(4-trifluoromethylphenyl)-3-pyrrolidino-1-propanone prepared in above (i) was treated in the same manner as in Example 9 (ii) and (iii) to give highly purified d-2-methyl-1-(4-trifluoromethylphenyl)-3-pyrrolidino-1-propanone hydrochride having a content of 99.5% or more, an optical purity of 99.5% or more, $[\alpha]_D^{20}$ of +44.8° (c=1.0, methanol) and a melting point of 156° to 159° C.

EXAMPLE 11 l-2-Methyl-1-(4-trifluoromethylphenyl)-3-pyrrolidino-1-propanone hydrochloride (i) In 65 ml of ethyl acetate were dissolved 14.3 g (50.0 mmol) of d -2-methyl-1-(4-trifluoromethylphenyl)-3-pyrrolidino-1-propanone and 9.66 g (50.0 mmol) of L-acetylphenylglycine ($[\alpha]_D^{20}$ = +212.8°, c=1.0, methanol). After the salt was formed, the solution was concentrated under reduced pressure to a residual amount of 27 g, and then was allowed to stand at room temperature for 7 days. To the solution was added with 45 ml of a 10% aqueous sodium chloride solution, 87 ml of ethyl acetate and 4.2 ml of aqueous ammonia and the ethyl acetate layer was extracted. The ethyl acetate layer was washed with 35 ml of a 10% aqueous sodium chloride solution and then dried over anhydrous magnesium sulfate. Subsequently, 12.5 ml of a 4N hydrochloric acid/dioxane solution was added to the ethyl acetate solution under cooling (25° C. or below). The resulting solution was concentrated under reduced pressure. To the residue was added 85 ml of ethyl acetate. The resulting solution was stirred at room temperature for 1 to 2 hours, and then the crystals were filtrated, and washed with ethyl acetate, and then dried under reduced pressure to give 14.80 g of l-2-methyl-1-(4-trifluoromethylphenyl)-3-pyrrolidino-1-propanone hydrochloride (content: 99%, optical purity: 92%).

(ii) The crude l-2-methyl-1-(4-trifluoromethylphenyl)-3-pyrrolidino-1-propanone hydrochloride prepared in above (i) was treated in the same manner as in Example 9 (ii) and (iii) to give highly purified l-2-methyl-1-(4-trifluoromethylphenyl)-3-pyrrolidino-1-propanone hydrochloride with a content of 99.5% or more, an optical purity of 99.5% or more, $[\alpha]_D^{20}$ of −44.8° (c=1.0, methanol).

EXAMPLE 13 l-2-Methyl-1-(4-trifluoromethylphenyl)-3-pyrrolidino-1-propanone hydrochloride (i) In 46 ml of hot acetone were dissolved 1.42 g (5.0 mmol) of dl-2-methyl-1-(4-trifluoromethylphenyl)-3-pyrrolidino-1-propanone and 0.67 g (5.0 mmol) of D-malic acid ($[\alpha]_D^{20}$ = +6.98°, c=1.0, methanol). After the salt was formed, the mixture was allowed to stand at room temperature. The crude crystals were filtered off and then recrystallized from acetone to give 0.263 g D-malic acid salt of l-2-methyl-1-(4-trifluoromethylphenyl)-3-pyrrolidino-1-propanone having an optical purity of about 96.6% and $[\alpha]_D^{20}$ of −27° to −28°, (c=1.0, methanol).

(ii) The D-malic acid salt of l-2-methyl-1-(4-trifluoromethylphenyl)-3-pyrrolidino-1-propanone prepared in above (i) was treated in the same manner as in Example 9 (ii) and (iii) to give highly purified l-2-methyl-1-(4-trifluoromethylphenyl)-3-pyrrolidino-1-propanone hydrochloride having a content of 99.5% or more and optical purity of 99.5% or more, $[\alpha]_D^{20}$ of −44.8° (c=1.0, methanol) and a melting point of 158° to 159° C.

EXAMPLE 14

1-(4-trifluoromethylphenyl)-2-methyl-3-piperidino-1-propanone (Compd. No. 5-1)

To a solution of 2.02 g of 1-(4-trifluoromethylphenyl)-1-propanone, 0.90 g of paraformaldehyde and 1.82 g of piperidine hydrochloride in 25 ml of isopropyl alcohol was added with 0.2 ml of concentrated hydrochloric acid. The mixture was refluxed under heating for 7 hours. The reaction solution was concentrated under reduced pressure to give the residue. To the resulting residue was added water and washed with ethyl ether. The aqueous layer was extracted with dichloromethane, and this dichloromethane layer was dried over anhydrous magnesium sulfate. The resulting crystal residue was recrystallized from a dichloromethane-ethyl acetate solvent to give 0.92 g of hydrochloride of Compd. No. 5-1 as colorless prisms, m.p. 197°–198° C.

NMR δ (CDCl₃, TMS): 1.20 (3H, d, J=7.5 Hz, —CH₃),

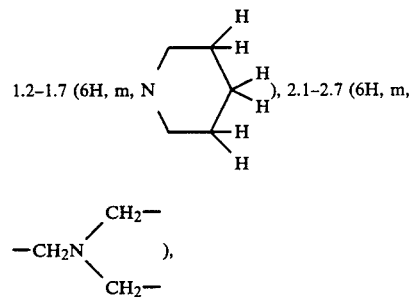

3.65 (1H, m, COC<u>H</u>), 7.70 (2H, d, J=9H, aromatic proton), 8.06 (2H, d, J=9H, aromatic proton)

IR $\nu_{max}^{KBr}$cm⁻¹: 1685 (CO)

Mass m/z (relative intensity): 299 (M⁺, 2.1), 214 (37.9), 173 (100), 145 (65.3)

The following compounds were obtained by following the process of Example 14.

| Starting compounds | | Objective compounds | | |
|---|---|---|---|---|
| Formula (II) | Formula (III) | No. | Yield %, | Melting point (°C.) |
| 1-(4-trifluoromethyl) butyrophenone | Piperidine | 5-2 | 25.6 (hydrochloride) | 178–179 (hydrochloride CH₂Cl₂—AcOEt) |
| 1-(4-trifluoromethyl) butyrophenone | Diethylamine | 5-3 | 34.4 (free base) | 110–112 (fumarate CH₂Cl₂—AcOEt) |

REFERENCE EXAMPLE 1

1-(2,3-Dimethylphenyl)-1-propanone

Two g of magnesium was added to 100 ml of anhydrous ether, and to this solution was added dropwise an anhydrous ether solution of 9 g of ethyl bromide. The resulting solution was stirred for 30 minutes and then 7.54 g of powdered cadmium chloride was added portionwise to said solution under cooling with ice water. Thereafter, the mixed solution was refluxed under heating for one hour to produce ethyl cadmium. After the reaction, ethyl ether was distilled off and 50 ml of benzene was added to the residue. To this mixed solution were added dropwise 9.3 g of 2,3-dimethylbenzoyl chloride, followed by refluxing under heating for one hour. The resulting reaction solution was poured into a mixture of ice water and dilute hydrochloric acid, and extracted with ethyl acetate. The ethyl acetate layer was dried over anhydrous magnesium sulfate. The drying agent was filtered out and the filtrate was concentrated under reduced pressure to obtain an oily product. This oily product was purified by silica gel column chromatography to give 1-(2,3-dimethylphenyl)-1-propanone as an oil.

Yield: 5.13 g (58%).

NMR δ(CDCl$_3$, TMS): 1.14 (t, 3H, J=8 Hz,

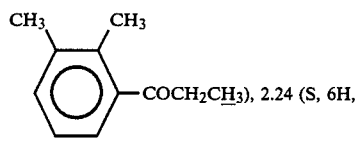, 2.24 (S, 6H,

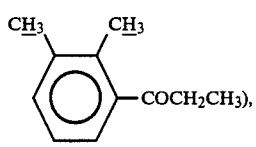, 2.74 (q, 2H, J=8 Hz, 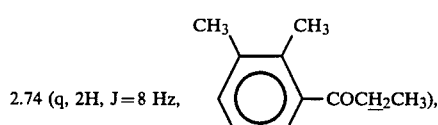, 6.8–7.5 (m, 3H, 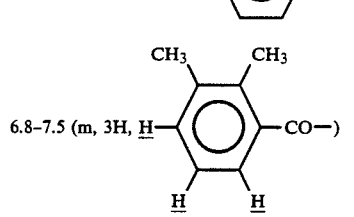

REFERENCE EXAMPLE 2

4-Methoxyl-5,6,7,8-tetrahydro-1-propionaphthone

A solution prepared by adding dropwise 4.27 g of propionic acid chloride to a solution of 6.16 g of anhydrous aluminum chloride in 70 ml of dichloromethane under ice cooling and stirring the mixture for 30 minutes was added dropwise to a solution of 6.24 g of 1-methoxyl-5,6,7,8-tetrahydronaphthalene in 20 ml of dichloromethane and further stirred at room temperature for 3 hours. The reaction solution was poured into ice water and extracted with dichloromethane. The dichloromethane layer was dried over anhydrous magnesium sulfate. The drying agent was filtered out and the filtrate was concentrated under reduced pressure to obtain 4-methoxyl-5,6,7,8-tetrahydro-1-propionaphthone in a yield of 7.94 g (94.5%).

IR $\nu_{max}^{neat}$: 1670 cm$^{-1}$

REFERENCE EXAMPLE 3

1-((4-Methoxyl)-5,6,7,8-tetrahydro-1-naphthyl)-2-butenyl-1-one

A solution prepared by adding dropwise 3.87 g of crotonoyl chloride to a solution of 4.94 g of anhydrous aluminum chloride in 50 ml of dichloromethane under ice cooling and stirring the mixture for 30 minutes was added dropwise to a solution of 5 g of 1-methoxyl-5,6,7,8-tetrahydronaphthalene in 20 ml of dichloromethane and further stirred at room temperature for 3 hours. The resulting reaction solution was poured into ice water and extracted with dichloromethane. The dichloromethane layer was dried over anhydrous magnesiuum sulfate. The drying agent was filtered out and the filtrate was concentrated under reduced pressure to obtain 6.95 g (98.0% yield) of 1-((4-methoxy)-5,6,7,8-tetrahydro-1-naphthyl)-2-butenyl-1one as an oily substance.

IR $\nu_{max}^{neat}$: 1660 cm$^{-1}$

REFERENCE EXAMPLE 4

1-(5,6,7,8-Tetrahydro-1-naphthyl)-1-propanone 0.963 g of propionealdehyde was added dropwise at room temperature to a Grignard solution prepared by adding 1-bromo-5,6,7,8-tetrahydronaphthalene in an amount of 1.75 g to 242 mg of magnesium in 20 ml of anhydrous ether, and the resulting solution was stirred at room temperature for one hour. The reaction solution was added with a saturated aqueous solution of ammonium chloride for decomposition and then extracted with ether. This ether layer was dried over anhydrous magnesium sulfate and filtered, and the filtrate was concentrated under reduced pressure to obtain 1.40 g of 1-(5,6,7,8-tetrahydro-1-naphthyl)-1-propanol as a crude oily product.

This product was dissolved in 20 ml of acetone, then added with a solution consisting of 72.5 ml of water and 4.72 g of chromic acid anhydride under ice cooling and stirred at room temperature for one hour. The reaction solution was concentrated under reduced pressure and, after distilling off acetone, extracted with ethyl acetate. The ethyl acetate layer was dried over anhydrous magnesium sulfate and filtered to remove the drying agent, and the filtrate was concentrated under reduced pressure to obtain 640 mg of 1-(5,6,7,8-tetrahydro-1-naphthyl)-1-propanone as an oily substance.

IR $\nu_{max}^{neat}$: 1690 cm$^{-1}$

REFERENCE EXAMPLE 5 i) 1-(4-trifluoromethylphenyl)butane-1-ol ii) 1-(4-trifluoromethylphenyl)butane-1-one 42.4 g of bromopropane was added dropwise to 8.4 g of metallic magnesium in 30 ml of dry ethyl ether, and then 30 ml of dry ethyl ether was further added. To this solution was added dropwise a solution of 20 g of 1-(4-trifluoromethyl)benzaldehyde in 60 ml of dry ethyl ether over a period of one hour. The mixed solution was then stirred at room temperature for one hour. The reaction solution was poured into an aqueous solution of ice and ammonium chloride and extracted with ethyl ether. The ethyl ether layer was dried over anhydrous magnesium sulfate and then filtered. The filtrate was evaporated under reduced pressure to give 21.9 g (87% yield) of 1-(4-trifluoromethylphenyl)-butane-1-ol as an oil.

21.9 g of 1-(4-trifluoromethylphenyl)butane-1-ol was dissolved in 300 ml of acetone, and to this solution was added dropwise a solution of 12.1 g of chromic anhydride in 205 ml of 7.5% sulfuric acid under ice cooling over a period of one hour. Thereafter, the mixture was stirred at room temperature for 3 hours. The solution was evaporated under reduced pressure. The residue was extracted with ethyl acetate and washed twice with water to obtain an ethyl acetate layer. This ethyl acetate layer was dried. The drying agent was filtered out and the filtrate was concentrated under reduced pressure. The residue was distilled under reduced pressure to give 17.1 g (79% yield) of 1-(4-trifluoromethyl)-butyrophenone as a light-yellow oily product having a boiling point of 65°–75° C. (under 1 mmHg). IR$\nu_{max}^{neat}$: 1680 cm$^{-1}$

What is claimed is:

1. An aminoketone derivative represented by the following formula (I):

or a pharmaceutically acceptable salt thereof, wherein R$^1$ is 4-trifluoromethylphenyl or 4-(C$_1$-C$_4$)alkoxy-5,6,7,8-tetrahydro-1-naphthyl, and one of R$^2$ and R$^3$ is a hydrogen atom and the other is (C$_1$-C$_4$) alkyl.

2. A propiophenone derivative represented by the following formula (II):

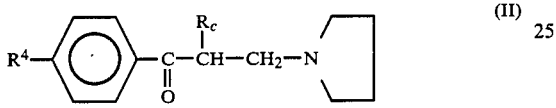

or a pharmaceutically acceptable salt thereof, wherein R$_c$ is C$_1$-C$_4$ alkyl and R$^4$ is trifluoromethyl.

3. An aminoketone derivative or a pharmaceutically acceptable salt thereof according to claim 1, wherein the compound of the general formula (I) is 1-(4-methoxy-5,6,7,8-tetrahydro-1-naphthyl)-2-ethyl-3-pyrrolidino-1-propanone.

4. An aminoketone derivative or a pharmaceutically acceptable salt thereof according to claim 1, wherein the compound of the general formula (I) is 1-(4-methoxy-5,6,7,8-tetrahydro-1-naphthyl)-2-methyl-3-pyrrolidino-1-propanone.

5. A propiophenone derivative or a pharmaceutically acceptable salt thereof according to claim 2, wherein R$_c$ is methyl or ethyl.

6. A propiophenone derivative or a pharmaceutically acceptable salt thereof according to claim 2, wherein the compound of the general formula (II) is 1-(4-trifluoromethylphenyl)-2-methyl-3-pyrrolidino-1-propanone.

7. A propiophenone derivative or a pharmaceutically acceptable salt thereof according to claim 2, wherein the compound of the general formula (II) is an l-isomer.

8. A propiophenone derivative or a pharmaceutically acceptable salt thereof according to claim 7, wherein the l-isomer is 1-2-methyl-1-(4-trifluoromethylphenyl)-3-pyrrolidino-1-propanone.

9. A pharmaceutical composition comprising a pharmaceutically effective amount of at least one of the derivatives or pharmaceutically acceptable salts thereof according to claim 1 or 2, and a pharmaceutically acceptable diluent or carrier.

10. A method for the treatment of spastic paralysis or the improvement of hypertonia of muscles in a homoisothermic animal, which comprises administering 0.1–20 mg/kg/day of an aminoketone derivative or a pharmaceutically acceptable salt thereof represented by the following formula to a homoisothermic animal having spastic paralysis or hypertonia of muscles:

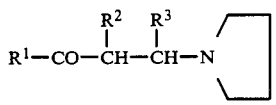

wherein R$^1$ is phenyl substituted by trihalogenmethyl, or 4-(C$_1$-C$_4$)alkoxy-5,6,7,8-tetrahydro-1-naphthyl, and one of R$^2$ and R$^3$ is a hydrogen atom and the other is (C$_1$-C$_4$) alkyl.

11. A method for the treatment of spastic paralysis or the improvement of hypertonia of muscles in a homoisothermic animal, which comprises administering 0.1–20 mg/kg/day of an aminoketone derivative represented by the following formula to a homoisothermic animal having spastic paralysis or hypertonia of muscles:

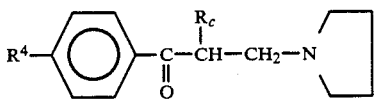

wherein R$_c$ is C$_1$-C$_4$ alkyl and R$^4$ is trihalogenmethyl.

* * * * *